US010806605B2

(12) United States Patent
Herr et al.

(10) Patent No.: US 10,806,605 B2
(45) Date of Patent: Oct. 20, 2020

(54) VARIABLE IMPEDANCE MECHANICAL INTERFACE

(71) Applicant: Massachusetts Institute of Technology, Cambridge, MA (US)

(72) Inventors: Hugh M. Herr, Somerville, MA (US); Andrew Marecki, Somerville, MA (US); David M. Sengeh, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 346 days.

(21) Appl. No.: 13/836,835

(22) Filed: Mar. 15, 2013

(65) Prior Publication Data
US 2013/0282141 A1   Oct. 24, 2013

Related U.S. Application Data

(60) Provisional application No. 61/612,572, filed on Mar. 19, 2012.

(51) Int. Cl.
*A61F 2/80* (2006.01)
*A61F 2/50* (2006.01)
(Continued)

(52) U.S. Cl.
CPC .............. *A61F 2/80* (2013.01); *A61F 2/5046* (2013.01); *A61F 2/78* (2013.01); *G06F 30/00* (2020.01);
(Continued)

(58) Field of Classification Search
CPC ........ A61F 2002/5047; A61F 2002/505; A61F 2002/5049
(Continued)

(56) References Cited

U.S. PATENT DOCUMENTS 4,735,754 A * 4/1988 Buckner ...................... 264/40.1
5,033,291 A   7/1991 Podoloff et al.
(Continued)

FOREIGN PATENT DOCUMENTS

EP          2 196 173 A2   6/2010
WO    WO 03/009787 A2    2/2003
(Continued)

OTHER PUBLICATIONS

YP Zheng, Arthur FT Mak, Aaron KL Leung, State-of-the-art methods for geometric and biomechanical assessments of residual limbs: a review, Journal of Rehabilitation Research and Development vol. 38 No. 5, Sep./Oct. 2001, 24 pages.*
(Continued)

*Primary Examiner* — Omar F Fernandez Rivas
*Assistant Examiner* — Robert S Brock
(74) *Attorney, Agent, or Firm* — Hamilton, Brook, Smith & Reynolds, P.C.

(57) ABSTRACT

A mechanical interface connecting a biological body segment, such as a limb, portion of a limb or other body segment, to a wearable device such as a prosthetic, orthotic or exoskeletal device, is fabricated by quantitatively mapping a characterized representation of the body segment to form a digital representation of the mechanical interface shape and mechanical interface impedance. The mechanical interface includes a continuous socket defining a contoured inside surface and a contoured outside surface, and includes a material having an intrinsic impedance that varies through the material, so that the intrinsic impedance varies along the contoured inside surface.

31 Claims, 17 Drawing Sheets
(15 of 17 Drawing Sheet(s) Filed in Color)

(51) Int. Cl.
  *A61F 2/78*  (2006.01)
  *G06F 30/00*  (2020.01)
(52) U.S. Cl.
  CPC ............... *A61F 2002/505* (2013.01); *A61F 2002/5047* (2013.01); *A61F 2002/5049* (2013.01)
(58) Field of Classification Search
  USPC .......................................................... 623/35
  See application file for complete search history.

(56) References Cited

U.S. PATENT DOCUMENTS

| | | | |
|---|---|---|---|
| 5,746,772 A * | 5/1998 | Jacobs | 623/35 |
| 5,993,400 A * | 11/1999 | Rincoe et al. | 600/595 |
| 6,585,774 B2 | 7/2003 | Dean et al. | |
| 6,804,571 B2 | 10/2004 | Fullen et al. | |
| 7,377,944 B2 | 5/2008 | Janusson et al. | |
| 8,005,651 B2 * | 8/2011 | Summit et al. | 703/1 |
| 8,323,353 B1 * | 12/2012 | Alley et al. | 623/33 |
| 8,423,167 B2 * | 4/2013 | Sanders et al. | 700/98 |
| 8,523,951 B2 * | 9/2013 | Kania | 623/36 |
| 8,551,184 B1 * | 10/2013 | Herr | 623/24 |
| 8,613,716 B2 * | 12/2013 | Summit et al. | 602/19 |
| 2002/0032485 A1 * | 3/2002 | Flam et al. | 623/23.51 |
| 2003/0216815 A1 * | 11/2003 | Christensen | A61F 2/7843 623/37 |
| 2004/0064195 A1 * | 4/2004 | Herr | 623/24 |
| 2004/0260402 A1 * | 12/2004 | Baldini | A61F 2/5046 623/33 |
| 2005/0119777 A1 * | 6/2005 | Arbogast et al. | 700/117 |
| 2007/0162153 A1 * | 7/2007 | Barnes et al. | 623/36 |
| 2010/0161076 A1 * | 6/2010 | Pallari | 623/36 |
| 2010/0262054 A1 * | 10/2010 | Summit et al. | 602/14 |
| 2010/0268135 A1 * | 10/2010 | Summit et al. | 602/12 |
| 2011/0082578 A1 * | 4/2011 | Stanhope et al. | 700/98 |
| 2012/0173001 A1 * | 7/2012 | Caspers | 623/34 |
| 2012/0271433 A1 | 10/2012 | Galea et al. | |
| 2013/0166256 A1 | 6/2013 | Wirx-Speetjens et al. | |
| 2013/0282141 A1 | 10/2013 | Herr et al. | |
| 2017/0290685 A1 * | 10/2017 | Montez | A61F 2/76 |
| 2018/0235779 A1 * | 8/2018 | Dudding | G06F 30/00 |
| 2019/0021880 A1 * | 1/2019 | Herr | A61F 2/5046 |

FOREIGN PATENT DOCUMENTS

| | | |
|---|---|---|
| WO | WO 2004/016158 A2 | 2/2004 |
| WO | WO 2006/092600 A1 | 9/2006 |
| WO | WO 13/142343 A1 | 9/2013 |
| WO | WO 2013/142343 A1 | 9/2013 |

OTHER PUBLICATIONS

Gabbiadini S, Knowledge-based design of lower limb prosthesis, PhD thesis, Industrial Engineering. University of Padova, Italy, 2011, See http://paduaresearch.cab.unipd.it/3771/, 181 pages.*
B. Rogers, A. Gitter, G. Bosker, M. Faustini, M. Lokhande and R. Crawford, "Clinical evaluation of prosthetic sockets manufactured by selective laser sintering", Proc. 12th Solid Freeform Fabrication Symp., pp. 505-512, 2001.*
Faustini, M.C.; Neptune, R.R.; Crawford, R.H.; Rogers, W.E.; Bosker, G., "An Experimental and Theoretical Framework for Manufacturing Prosthetic Sockets for Transtibial Amputees," Neural Systems and Rehabilitation Engineering, IEEE Transactions on, vol. 14, No. 3, pp. 304-310, Sep. 2006.*
Silver-Thorn MB, Steege JW, Childress DS . A review of prosthetic interface stress investigations . J Rehabil Res Dev 1996 ;33(3) :pp. 253-266.*
Fan Gao, Zhigang Wang, and Xin Lei, Finite Element Analysis Based Design Optimization for Prosthetic Socket, Annual Meeting of the American Society of Biomechanics, 2009, 2 pages.*
Sara S. P.Marreiros, Skin Strain Field Analysis of the Human Ankle Joint, MS Thesis, University of Lisbon, 2010, 93 pages.*
G R Liu and Nguyen Thoi Trung, Smoothed Finite Element Methods, Chapter 3, CRC Press 2010, pp. 31-82.*
Colombo, Giorgio, Stefano Filippi, Caterina Rizzi, and Federico Rotini. "A new design paradigm for the development of custom-fit soft sockets for lower limb prostheses." Computers in Industry 61, No. 6 (2010): 513-523.*
Rosen, Jacob, and Mircea Arcan. "Modeling the human body/seat system in a vibration environment." Journal of biomechanical engineering 125, No. 2 (2003): 223-231.*
Tonuk, Ergin, and M. Barbara Silver-Thorn. "Nonlinear viscoelastic material property estimation of lower extremity residual limb tissues." Journal of biomechanical engineering 126, No. 2 (2004): 289-300.*
Kerem Usu. "Identification of Soft Tissue Mechanical Material Model and Corresponding Parameters From In Vivo Experimental Data by Using Inverse Finite Element Method." PhD diss., Middle East Technical University, 2008.*
Moes, Cornelis Christian Marie. Advanced human body modelling to support designing products for physical interaction. TU Delft, Delft University of Technology, 2004.*
Roberto Morotti, Development of a Virtual Testing Laboratory for Lower Limb Prosthesis, Thesis, Universita degli Studi di Padova, 133 pages, (2014).*
Goh, J. C. H., P. V. S. Lee, S. L. Toh, and C. K. Ooi. "Development of an integrated CAD-FEA process for below-knee prosthetic sockets." Clinical Biomechanics 20, No. 6 (2005): 623-629.*
Rogers, Bill, Gordon Bosker, Mario Faustini, Gail Walden, Richard R. Neptune, and Richard Crawford. "Case report: variably compliant transtibial prosthetic socket fabricated using solid freeform fabrication." JPO: Journal of Prosthetics and Orthotics 20, No. 1 (2008): 1-7.*
Herr, Hugh. "Exoskeletons and orthoses: classification, design challenges and future directions." Journal of neuroengineering and rehabilitation 6, No. 1 (2009): 1-9.*
International Search Report and Written Opinion of the International Searching Authority for corresponding PCT/US2013/032190, entitled "Variable Impedance Mechanical Interface," dated Jun. 25, 2013.
Vannah, William M., and Childress, Dudley S., "Indentor tests and finite element modeling of bulk muscular tissue in vivo," *J. Rehab. Res. Dev.*, 33(3):239-252 (1996).
International Preliminary Report on Patentability from International Application No. PCT/US2013/032190, "Variable Impedance Mechanical Interface," dated Oct. 2, 2014.
Charalambides et al.; "A Novel All-Elastomer MEMS Tactile Sensor for High Dynamic Range Shear and Normal Force Sensing," J. Micromech. Microeng. 25(9): (9 pages) (Aug. 2015).
Dagdeviren et al.; "Conformal Piezoelectric Systems for Clinical and Experimental Characterization of Soft Tissue Biomechanics," Nature Materials, 14, pp. 728-736 (Jul. 2015).
U.S. Appl. No. 62/278,158, filed Jan. 13, 2016; "Automated Computational Framework for the Design of Human-Specific Mechanical Interfaces that Connect a Device to a Biological Body Segment"; Herr et al.
U.S. Appl. No. 62/377,128, filed Aug. 19, 2016; "Automated and Data-Driven Computational Design of Patient-Specific Biomechanical Interfaces"; Herr et al.
Invitation to Pay Additional Fees from International Application No. PCT/US2017/013154, "Method and System for Designing a Biomechanical Interface Contacting a Biological Body Segment," dated Apr. 19, 2017.
Notification of Transmittal of the International Search Report and the Written Opinion of the International Searching Authority, or the Declaration, for PCT/US2017/013154, entitled "Method and System for Designing a Biomechanical Interface Contacting a Biological Body Segment,", dated Jun. 19, 2017.

* cited by examiner

Detail B

Detail A

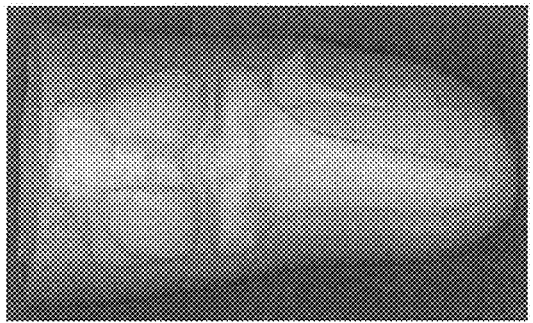
FIG. 13D
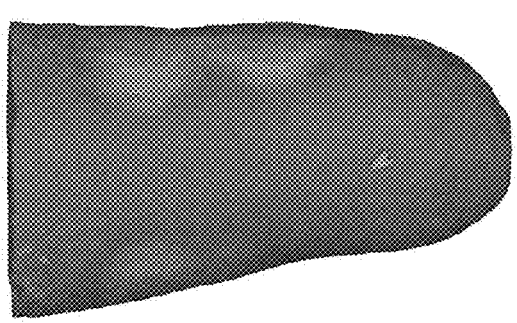
FIG. 14D
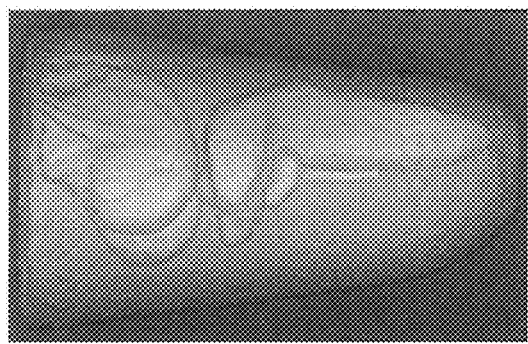
FIG. 13C
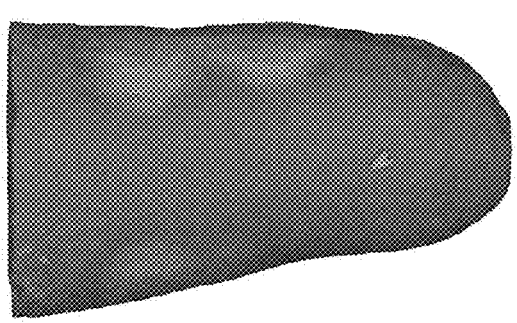
FIG. 14C
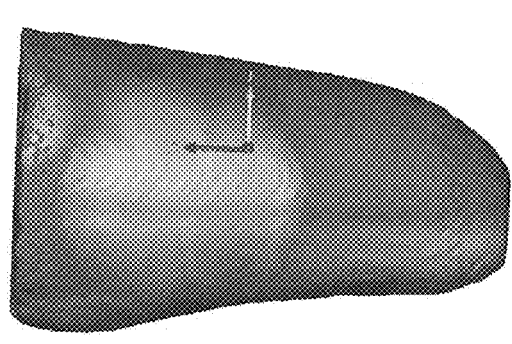
FIG. 13B
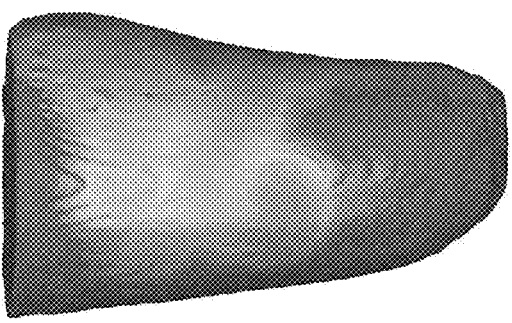
FIG. 14B
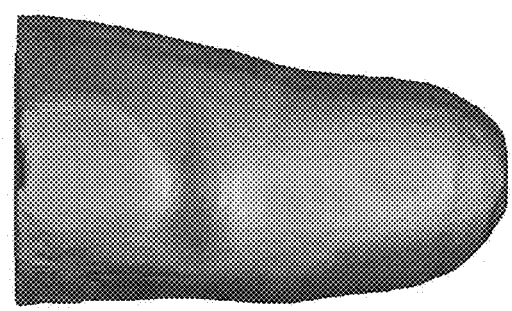
FIG. 13A
FIG. 14A

| Soft Tissue Depth (mm) | Color | Socket Tensile Strength (MPa) | Color |
|---|---|---|---|
| 0 – 9 |  | 0.5 – 1.5 |  |
| 9 – 13 |  | 8 – 12 |  |
| 13 – 16 |  | 12 – 14 |  |
| 16 – 20 |  | 14 – 20 |  |
| 20 – 50 |  | 50 – 65 |  |

FIG. 17

VARIABLE IMPEDANCE MECHANICAL INTERFACE

This application claims the benefit of U.S. Provisional Application No. 61/612,572, filed on Mar. 19, 2012. The entire teachings of the above application are incorporated herein by reference.

BACKGROUND OF THE INVENTION

Prosthetics, orthotics and exoskeletons often are custom-made to conform to a limb, vestigial limb or body segment of interest by obtaining a mold of a vestigial limb or body segment of interest and then fabricating a socket to conform to that vestigial limb of body segment of interest. Often, in order to transfer load, the socket is of a rigid material that typically is homogeneous, or nearly homogeneous and meets physical properties necessary to transfer the load. For example, such sockets are commonly formed of carbon fiber and are essentially rigid across the entire surface of the socket interfacing with the minimum body segment with which it is in contact.

Conventional design and fabrication strategies for mechanical interfaces typically employ an incomplete data representation of the relevant human body segment, and a non-quantitative methodology to determine the corresponding interface design. Furthermore, known interface fabrication strategies generally do not allow for continuously varying material properties within the interface that reflect the multi-tissue, continuously-varying, viscoelastic properties of the underlying anatomy for which the mechanical interface is designed to intimately connect.

Generally, a prosthetist first takes a mold of the residual limb, capturing its 3-D shape. Depending on the practitioner's preference, this molding process is performed when the relevant human body segment is either in a loaded or unloaded state. The measurement of residual limb shape is most typically performed using a plaster-impregnated gauze that is first dipped into water and then wrapped around the residual limb. Once wrapped, the plaster hardens to form a female cup that is then poured with plaster to form a male plug with the residual limb's shape. The prosthetist then removes plaster in soft tissue regions where he/she wants the final socket interface to compress the residual limb tissue, and adds plaster around sensitive regions to create a void in the final socket wall. Once these craft modifications are complete, a final carbon composite or thermoplastic socket is fabricated over the male plug. The final interface is typically homogenous, or nearly homogenous in its viscoelastic, spatial and temporal properties.

The limb or body segment contacting prosthetic or orthotic devices are not, however, homogeneous in the physical properties associated with load bearing and transfer of force from the limb or body segment to the prosthetic or orthotic during use. For example, the surface of the limb or body segment contacting a prosthetic device varies continuously, not only in shape, but in impedance, as measured orthogonally to the tissue surface, by virtue of variability in soft tissue depth, tissue distribution, tissue density, viscoelasticity, skin tensile strain, neural activation and sensitivity of the limb or body segment during changes in limb or body segment position, and load bearing by the limb or body segment. Failure to accommodate variability in the physical properties of a limb or body segment and use of the prosthetics/orthotics can cause extreme discomfort and sharply limits the utility of the device.

Attempts to ameliorate the problems associated with consequent on uneven distribution of load bearing at the interface between a limb or body segment and a prosthetic or orthotic device include, for example, fitting of a liner between the limb body segment and the prosthetic or orthotic surface to minimize the effect of variability in orthogonal impedance of the limb or body segment at the interface with the prosthetic or orthotic device. Typically, the liner has an orthogonal impedance that is much lower than that of the prosthetic or orthotic device, and includes an internal surface fabricated to maximize tactile comfort, thereby minimizing chafing at portions of the limb or body segment where orthogonal impedance of the limb or body segment and load bearing at the interface between the limb or body segment in the prosthetic or orthotic device are relatively high. Such attempts, however, do not reflect the continuously-varying impedance and skin strain field of the underlying anatomy and consequently often cause the prosthetic or orthotic device to have an uneven pressure distribution with excessive shear and pressure points, thereby limiting the physical activity of the subject wearing the prosthetic or orthotic device.

Another attempt to reduce problems associated with multi-tissue, continuously-varying, viscoelastic properties of the underlying anatomy of mechanical interfaces between body segments and prosthetic, orthotic and exoskeletal devices, includes using a 'windowing' approach where holes are cut into a rigid, external interface wall to allow an intermediate, softer material to penetrate through the window upon load bearing applied to the interface. However, such windowing techniques use separate distinct material components resulting in an interface that does not reflect the continuously-varying human body viscoelastic properties found in the underlying anatomy. Well-known techniques typically only approximately reflect the continuously varying viscoelastic properties of tissue affected by prosthetic, orthotic and exoskeletal devices when in use.

Therefore, there is a need for a mechanical interface connecting the human body limb or body segment to a wearable device that overcomes or minimizes the above-referenced problems.

SUMMARY OF THE INVENTION

The invention generally is directed to a mechanical interface and to a method for fabricating a mechanical interface connecting a biological body segment, such as a limb, portion of a limb, or torso segment, to a wearable device.

In one embodiment of the invention, the mechanical interface for connecting a biological body segment to a wearable device includes a continuous socket defining a contoured inside surface and, optionally, a contoured outside surface. The socket includes a material having an intrinsic impedance that varies spatially through the material, whereby the intrinsic impedance varies along the contoured inside surface and, optionally, along a contoured outside surface.

In one specific embodiment, the mechanical interface of the invention further includes a relatively rigid open shell mated to the socket, wherein the shell defines an interior surface that supports the socket. In another specific embodiment, the socket defines an outside surface that, in combination with the interior surface of the shell, defines, at least in part, at least one gap between the inside surface of the shell and the outside surface of the socket. The size of the gap can be inversely proportional to the intrinsic impedance of the material of the portion of socket defining the surface of the socket at the gap. For example, in one embodiment, the size of the gap is defined by the orthogonal distance between the outside surface of the socket and the inside surface of the shell.

In yet another embodiment, the invention is a method for fabricating a mechanical interface for connecting a human body segment, such as a vestigial limb or portion of a body segment, to a wearable device. The wearable device can be, for example, a prosthetic, orthotic or exoskeletal device. The method includes compiling a data set of features corresponding to the biological body segment. The compiled data set is then processed to thereby form a characterized representation of the body segment. The characterized representation of the body segment is quantitatively mapped to form a digital representation of a mechanical interface shape and a mechanical interface impedance. A mechanical interface is then fabricated that correlates to the digital representation of the mechanical interface shape and the mechanical interface impedance to thereby form the mechanical interface for connecting the biological body segment to the wearable device.

The present invention has many advantages. For example, the mechanical interface of the invention has an orthogonal impedance that varies inversely to the orthogonal impedance of the body segment contacting the mechanical interface during use of a wearable device, such as a prosthetic, orthotic or exoskeletal device. By inversely varying the orthogonal impedance relative to that of the body segment, the prosthetic, orthotic or exoskeletal device can transfer load effectively from the subject to the prosthetic, orthotic or exoskeletal device while minimizing shear stress and peak pressure at the interface between the subject and the prosthetic, orthotic or exoskeletal device. In addition to significantly reducing the amount of work lost during transfer of force from the subject to the prosthetic, orthotic or exoskeletal device, comfort of the subject wearing the device is significantly increased. Consequently, the utility of the prosthetic, orthotic or exoskeletal device is also significantly increased without the necessity of having to employ a sock or liner at the mechanical interface. Optionally, or alternatively, a sock or liner can be employed that, in itself, varies in orthogonal impedance inversely with that of the subject at the mechanical interface with the body segment of the subject.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 10B and 10C show the orthogonal distance D between the unloading skin surface and a bone intersection, or the soft tissue depth. Red regions show large tissue depths, yellow regions show moderate depths and green regions show small depths. For these depth models, the patella tendon was removed, exposing soft tissue depth in the region of the patella tendon just distal to the patella (shown as the red region in FIG. 10B).

FIGS. 13A-13D represents MRI images of a right residual limb of the trans-tibial amputee.

FIGS. 14A-14D represents soft tissue depths of the right residual limb of the trans-tibial amputee corresponding to the images of FIGS. 13A-13D, respectively.

FIG. 17 is a table of color mapping used in FIGS. 14A-14D, and FIGS. 15A-15D. Soft tissue depth is shown in millimeters (mm) and socket tensile strength in Mega-Pascals (MPa).

DETAILED DESCRIPTION OF THE INVENTION

A description of example embodiments of the invention follows.

The invention generally is directed to a method for fabricating a mechanical interface connecting a biological body segment to a wearable device, and to a mechanical interface for connecting a biological body segment to a wearable device. The invention employs a quantitative scientific methodology that includes measurements, such as biological segment shape, viscoelastic tissue properties, vascularization anatomy, nerve sensitivities and skin strain characteristics during joint movements, to generate an interface having corresponding shape and impedance characteristics, both spatially and temporally. It will be understood by those of skill in the art that the methodologies presented can be employed in the mechanical-interface design and fabrication of any wearable mechanism, including prosthetic, orthotic and exoskeletal devices.

Figure 1:
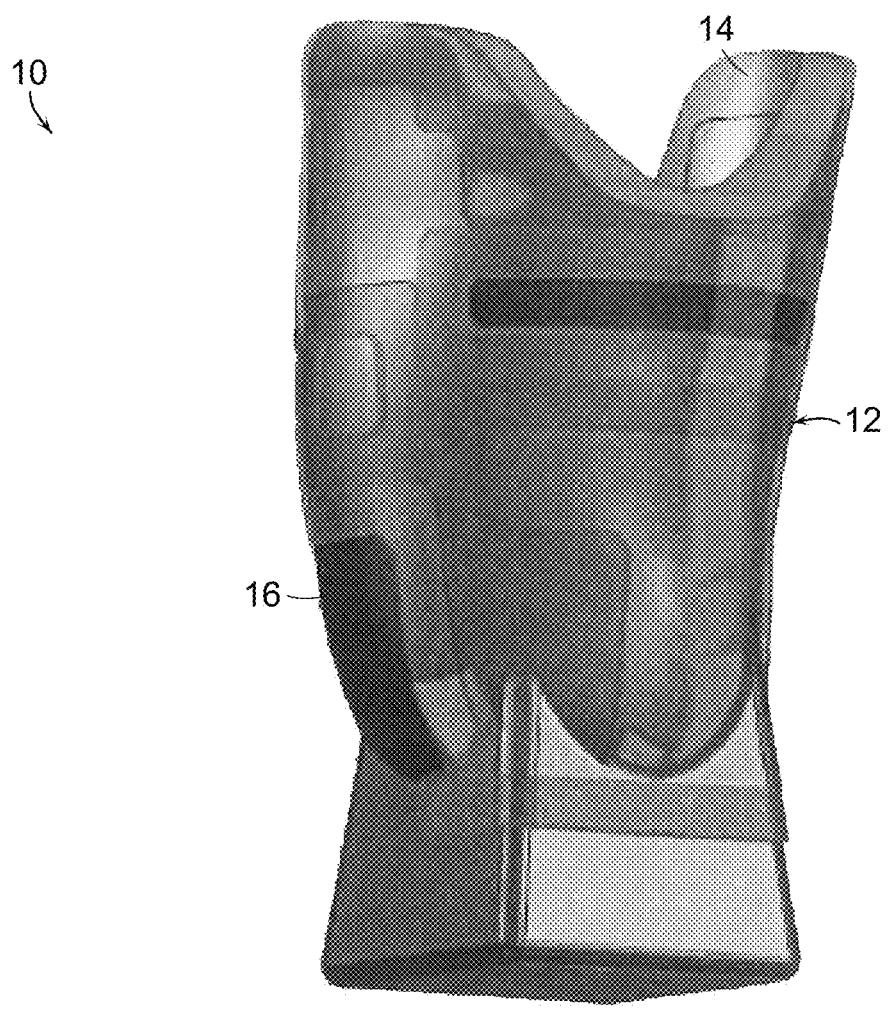
FIG. 1 is a perspective view of an embodiment of a mechanical interface of the invention.

In one embodiment, the mechanical interface 10 of the invention, shown in FIG. 1, includes continuous socket 12 defining a contoured inside surface 14 and a contoured outside surface 16. Socket 12 includes a material having intrinsic impedance that varies through the material, whereby intrinsic impedance varies along the contoured inside surface and the outside surface. Suitable body segments for use with a mechanical interface of the invention include, for example, biological body segments of humans, such as limbs and vestigial portions of limbs. Other suitable body segments can include, for example external portions of a human torso, or any load-bearing surface of a human. Examples of suitable wearable devices to be connected to a biological body segment by a mechanical interface of the invention include prosthetics, orthotics and exoskeletal devices, such as prosthetics, orthotics and exoskeletons employed to substitute for, or support, human limbs and portions of human limbs.

Figure 2:
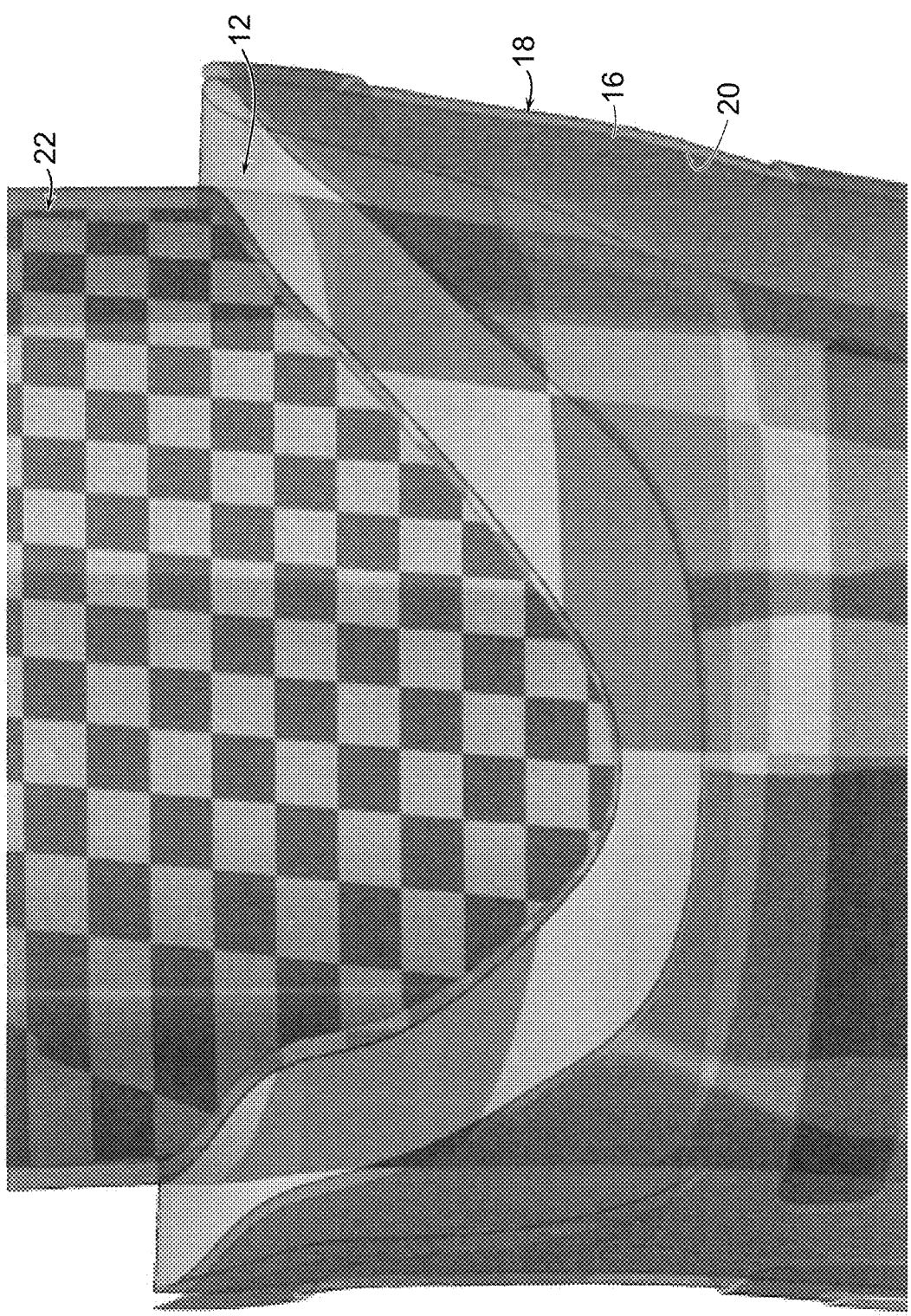
FIG. 2 is a partial view of a mechanical interface of the invention, including a liner within a socket, and an outside shell supporting the socket.

In another embodiment, shown in FIG. 2, mechanical interface 10 further includes relatively rigid open shell 18 mated to socket 12. Shell 18 defines interior surface 20 that supports socket 12. Liner 22 is within socket 12 and contacts inside surface 14 of socket 12. In one embodiment, liner 22 includes a plurality of materials. Examples of suitable materials of liner 22 include silicone, polyurethane or other polymers known in the art. Typically, materials of liner 22 include a relatively thin and/or relatively compliant material, proximate to portions of a body segment where relatively large skin tensile strains occur, and relatively thick and/or stiff materials proximate to portions of the body segment where skin tensile strains are relatively small. In a particular embodiment, liner 22 includes strips of material running transversely to a general direction of skin tensile strain of a portion of the body segment most proximate to each individual strip.

Examples of suitable materials of socket 12 include silicone, polyurethane, materials formed through a shape deposition process, or 3-D printed polymers or composite materials. Examples of suitable materials of shell 18 include carbon fiber, fiberglass, or any other composite material known in the art. Shell 18 typically is essentially rigid relative to the socket.

Figure 3B:
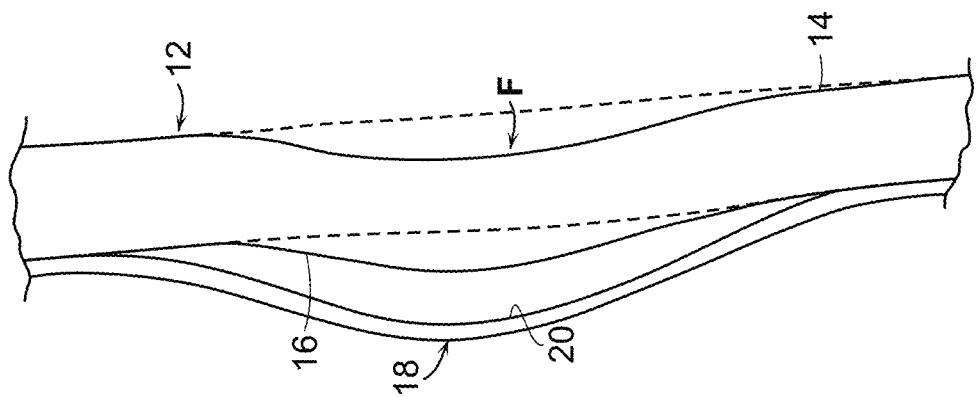
FIG. 3B is a detail of the cross-section of the socket and shell of FIG. 3A depicting reduction in the size of the gap of FIG. 3A upon application of orthogonal force on the inside surface of the socket.
Figure 3A:
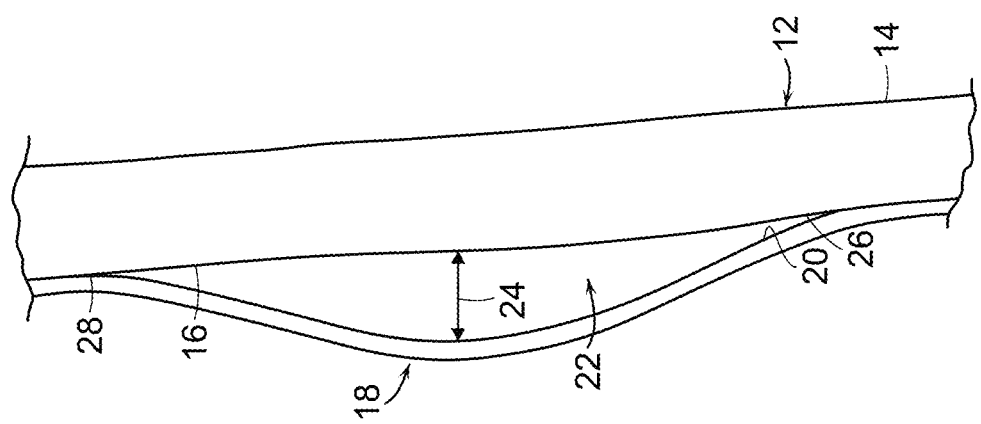
FIG. 3A is a detail of a cross-section of a socket and shell of the invention depicting a gap between a portion of the socket and the shell

A cross-sectional view of a portion of mechanical interface 10 shown in FIG. 2 can be seen in FIGS. 3A and 3B. As shown therein, outside surface 16 of socket 12, in combination with interior surface 20 of shell 18, defines, at least in part, at least one gap 22 between inside surface of shell and outside surface of socket. The size of gap 22, as measured orthogonally to the outside surface 16 of socket 12 from one end 26 of gap 22 to another end 28 of gap 22 varies continuously, as can be seen by the length of arrow 24 as arrow 24 moves through gap 22 from end 26 to end 28. The maximum size of at least one gap is inversely proportional to the intrinsic impedance of the material of the portion of socket defining outside surface 16 of socket 12 at gap 22. As orthogonal force F is applied to inside surface of socket 12 by a body segment, gap 12 is diminished in size, as can be seen in FIG. 3B.

Figure 4:
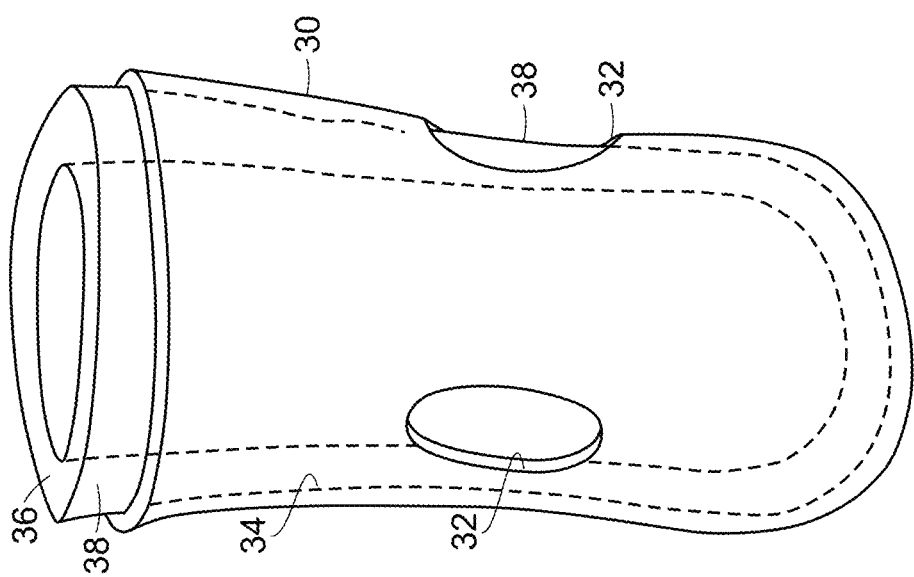
FIG. 4 is a perspective view of one embodiment of a mechanical interface of the invention defining opening in a shell of the interface proximate to a portion of the socket having relatively low orthogonal impedance.

In another embodiment, shown in FIG. 4, open shell 30 defines at least one opening 32 along inside surface 34 of shell 30. Openings 34 defined by shell 30 extend about portions of outside surface 38 of socket 36 having low orthogonal impedance relative to orthogonal impedance of adjacent portions of outside surface 38 of socket 36. In one embodiment, areas of openings 34 defined by a shell 30 are inversely proportional in size to the orthogonal impedance of socket 36 at openings 34 of shell 30.

Figure 5:
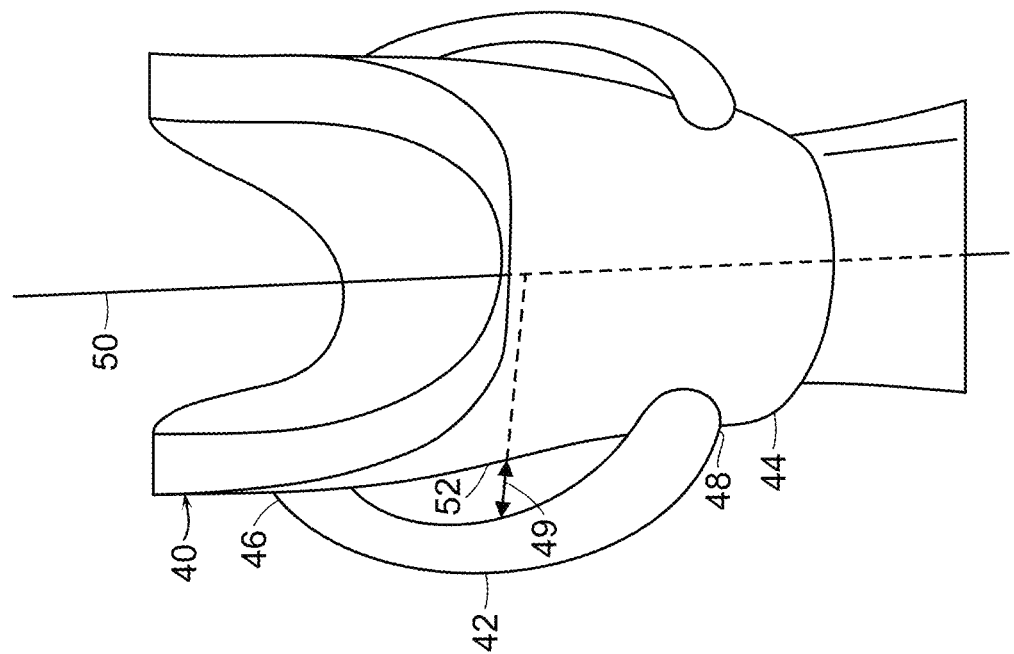
FIG. 5 is a perspective view of one embodiment of the mechanical interface of the invention having struts instead of a shell supporting a socket.

FIG. 5 represents an embodiment of socket 40 that includes at least one strut 42 that is linked to the remainder 44 of socket 40 at either end 46,48 of strut 42, whereby strut 42 and remainder 44 of socket 40 define gap 49. In one embodiment, gap 49 extends generally orthogonally from major longitudinal axis 50 of the device. In one embodiment, the size of gap is inversely proportional to the intrinsic impedance of the remainder of socket 40 at gap 49. Typically, strut 42 is rigid relative to portion 52 of the socket 40 opposite strut 42 at gap 49, wherein the strut connects a relatively stiff socket region to another socket region of similarly high stiffness to effectively transfer mechanical load during weight bearing.

In still another embodiment, the mechanical interface of the invention defines a surface, wherein the surface has a mechanical property that is distinct from that of the remainder of the mechanical interface. For example, the mechanical property of the surface of the mechanical interface that varies continuously across the mechanical interface can be that of response to tensile strain, or tensile impedance. In one particular embodiment, the response to tensile strain of surface is inversely proportional to changes in skin tensile strain of a most proximal portion of a body segment of the subject wearing a device that employs the mechanical interface of the invention.

In one embodiment, the design and fabrication methodologies of the present invention are divided into four different phases or steps. The first step includes acquiring a comprehensive data set of the relevant human body segment's underlying anatomy and biomechanics for which the mechanical interface will connect. In a second step, these biological data are processed and a mathematical model generated, to fully characterize the human limb with a model or digital representation. In a third step, a quantitative mapping from the biological model to an interface model is generated that describes the digital representation of interface shape and dynamic properties. In a fourth step, the interface model is used to fabricate either a test interface or the final interface to be used by the wearer of the prosthetic, orthotic, or exoskeletal mechanism.

STEP 1: A method of the invention for fabricating a mechanical interface connecting a biological body segment to a wearable device includes compiling a data set of features corresponding to the biological body segment. The data set is compiled by, for example, employing at least one method selected from the group consisting of casting, surface scanning, computerized tomography, magnetic resonance imaging, magnetic resonance elastography, ultrasound, photogrammetography and electromechanical measurement tools.

Specifically, the first part to the production of a mechanical interface includes collecting anatomical and biomechanical data that can be used to develop a model of the biological segment of interest (Step 2). Such a model is necessary to describe the relevant biological segment's properties, including but not limited to, its shape, viscoelastic tissue properties, vascularization anatomy, nerve sensitivities, and skin strain characteristics during body movements—all as a function of anatomical location.

For example, tissue impedance is estimated using a suitable measurement, such as by at least one member of the group consisting of: orthogonal force; displacement and speed of displacement of a probe applied to the body segment; soft tissue depth, skin tensile strain; compression strain; compression damping, compression stiffness; and percent soft tissue compression measured at each node employed to generate the anatomical and biomechanical model.

In another example, the human anatomy is imaged and digitized with a liner, socks or other clothing accessories that would be used with the interface design. In such an approach, the interface is designed to fit over said liner, socks and/or other clothing accessories. In another embodiment, the biological limb is imaged without such accessories, and the resulting mechanical interface constitutes the totality of the interface worn by the wearer.

The comfort of a mechanical interface is, in part, dependent on the quality of the volumetric data acquired of the residual limb. Methodologies that have been used to capture the shape of the residual limb include casting, surface scanning and more advanced imaging techniques including Computerized Tomography (CT) and Magnetic Resonance Imaging (MRI).

In one embodiment, The FastSCAN™ system produced and supplied by Polhemus (40 Hercules Dr, Colchester, Vt. 05446, USA, T: 800-357-4777) is used to measure the shape of the relevant human body segment. This system may be used because of its convenience and accuracy. Setup and scan time is about five minutes and the scanning tool is easy to use. The system is lightweight and connected to a computer monitor—making it ideal to see the results in real time. Images are exported from the FastSCAN™ software in STL format.

Other tools can be used to capture the shape of the relevant human limb segment including digitizers. Sanders et al. developed a mechanical digitizer specifically for use in prosthetic socket research. Commercially available digitizers exist, such as, the Provel d2 Digitizer™, which is made specifically to capture the external shape of a human body segment. The latter digitizer exports files in the AOP format used by most prosthetists and this could be converted to STL formats and other CAD file formats using third party software.

Magnetic Resonance Imaging (MRI):

Using Nuclear Magnetic Resonance (NMR), it is possible to spatially map the distribution of the Hydrogen atoms in a body segment. MRI is a non-invasive imaging technique that relies on the magnetic properties of the nucleus in Hydrogen atoms. A three-Tesla MRI machine uses the high magnetic field to align the magnetic Hydrogen atoms within water molecules within the body. Radio waves of known frequencies are then applied to the body causing the magnetic particles within the Hydrogen atoms to change their orientation from the direction of the magnetic field applied by the magnet in the scanner. The spin of the hydrogen nuclei is detected by a sensitive radio and this information is processed to generate a magnetic resonance image.

In one embodiment, the use of MRI data is employed as a means of acquiring a comprehensive digital representation or model of the biological limb, including but not limited to external biological limb shape, soft tissue depth, tissue locations and densities, and the viscoelastic tissue properties at each anatomical location across the biological limb.

As such, MRI can be used to generate 2D and 3D reconstructions of the different tissues found in the biological limb of interest. Furthermore, the surface geometry image generated by MRI may be used to supplement, or replace, surface images captured using other scanners.

MRI Sequence:

The quality of the image developed depends on the type of sequences run on the MRI machine. The pulse sequence is the computer program that affect how and what signal frequencies are emitted to and captured from the body by controlling the hardware of the MRI system. A pulse sequence consists of predefined gradient of radio frequencies used during a scan.

MRI Coil Used:

An MRI coil is made of conductive material looped around the core of the coil. The coil serves a dual function: creating and detecting magnetic fields around a specific area that is being imaged. There are different types of coils depending on the type of body or object to be imaged. For the residual limb of an amputee, extremity coils are favorable. For example, known specific coils for knees are usually long enough to capture the full length of a transtibial residual limb and have a large field of measurement. Furthermore the inner diameter of the coil is large enough to house the residual limb while being small enough to allow for good quality images.

MRI Data Processing and Export:

MRI data are generated based on the spatial distribution of the frequency and phase of proton magnetization. The primary format for all MRI files is the Digital Imaging and Communications in Medicine (DICOM) standard for distributing and viewing medical images. DICOM images can be opened and modified in various image-processing platforms. From these .STL formats can be created other formats (e.g. Solid Works) for further computer-aided design and manufacture. In addition to digital scanners and MRI imaging strategies, other imaging tools can be employed to acquire a representation of the biological limb including, but not limited to, ultrasound and standard photogrammetric tools. Further, in one embodiment, an electromechanical device can be employed to directly measure the external biological limb shape and the viscoelastic tissue properties at each anatomical location across the biological limb. Such a device measures force as a function of compression, and velocity of compression, for orthogonal displacements of the tissue at each anatomical point on the biological limb. Such a mechanism can be employed to generate an accurate and data rich representation of the biological limb.

MRE:

MR Elastography (MRE) is based on Magnetic Resonance Imaging (MRI). MRE is a technique to assess the mechanical properties of anatomical tissues. In MRE, shear waves (sound waves) are propagated into the soft tissues and the resulting tissue deformation is imaged using a phase-contrast MRI sequence. The images acquired are post processed by employing inversion algorithms to represent a relative display of tissue stiffness. While MRE has been applied to a great extent at soft tissues and organs internal to the human body (liver, spleen, breast, kidney, brain, cardiac, etc), MRE can be employed to characterize the quantitative soft tissue as a mechanical property at each location on the residual limb. This approach can be combined with MRI in the design of data-driven comfortable interfaces. MRI as a technique provides the three dimensional shape of a residual limb and a spatial representation of bone depth at each location on the limb. Soft tissue (muscles and bones) are also segmented with an accurate representation of their cross fiber tissue thickness. A combination of skin thickness, muscle and fat tissue thickness give overall bone depth from the surface of the skin. Soft tissue models that provide estimates of Shear modulus and consequently Young's modulus can be developed based on MRI and MRE measurements. Such quantitative data are then employed to design the mechanical interfaces for the body.

Electromechanical Measurement Tools:

Electromechanical tools can also be used to estimate stiffness and damping of body tissue through physical contact with the biological body segment. In one embodiment, this can be accomplished through three processes. First, the tissue is measured by actuators through a series of controlled interactions that deflect the tissue. Second, the data—position and force with respect to time—is conditioned for system identification purposes. Lastly the data are employed to identify a linear or non-linear transfer function which describes the physical response of the tissue to a given load (force) or deflection.

The collected data consist of positions and forces that are referenced to time. This time reference allows velocity and acceleration to be calculated as well. In order to identify the system, we will look at the input versus the output of the system. For example, the input is X(t) and the output is Y(t), in order estimate the linear transfer function, the input function X(t) to get $X_{ac}(t)$. The input and output are then correlated to get $XY_{cc}(t)$. Toeplit matrix is formed with $X_{ac}(t)$: TP(t). Then, the impulse response function of the system, h, is $F_s(TP(t)^{-1} \cdot XY_{cc}(t))$. Where $F_s$ is the frequency of the samples and $TP(t)^{-1}$ is the inverted Toeplitz matrix. Given a linear system, the parameters of the transfer function can be determined from the impulse response.

Stiffness data can be collected using a ring of linear actuators that surround the measurement area. This ring is capable of measuring every point on the ring at the same time. Between 1 and 50 points (or as many as space allows) can be measured simultaneously with this method. Each linear actuator is independently controlled with its own force and position sensors.

STEP 2: The compiled data set is then processed to thereby form a characterized representation of the body segment. In one embodiment, the compiled data set is processed to generate at least one anatomical and biomechanical model of nodes of data, wherein each node includes a subset of data. The model collectively represents tissue impedance and at least one member of the group consisting of external biological body segment shape, soft tissue depth, tissue distribution, tissue density, viscoelasticity, skin tensile strain, and neural muscle activation and sensitivity to externally applied pressure influenced by underlying anatomy of the body segment.

In one embodiment, a subset of data of at least a portion of the nodes includes external biological body segment shape and orthogonal impedance of the body segment. The body segment may or may not be under any external load. In a particular embodiment, the subset of data for each node is generated by: marking a surface of the body segment to form a detectable matrix of nodes; quantitatively mapping the nodes; measuring orthogonal impedance of the body segment at each node; moving the body segment, thereby cause the markings to redistribute relative to each other; and quantitatively mapping the redistributed markings to thereby generate a three-dimensional image of redistribution of markings that corresponds to skin tensile strain of the body segment; and re-measuring the orthogonal impedance of the body segment at least a portion of the nodes. In one embodiment, the three-dimensional image is a photogrammetric image. In another embodiment, the markings are processed as point clouds, wherein the point clouds are triangulated. In a particular embodiment, the triangulated point clouds are processed by constant strain element analysis.

In particular, an anatomical and biomechanical model can be generated, including but not limited to, external biological limb shape, soft tissue depth, tissue locations and densities, and/or the viscoelastic tissue properties for orthogonal tissue compressions at each anatomical location across the biological limb. Further, using standard photogrammetric tools, a model of skin strain as a function of anatomical location and joint pose can be generated.

Figure 6C:
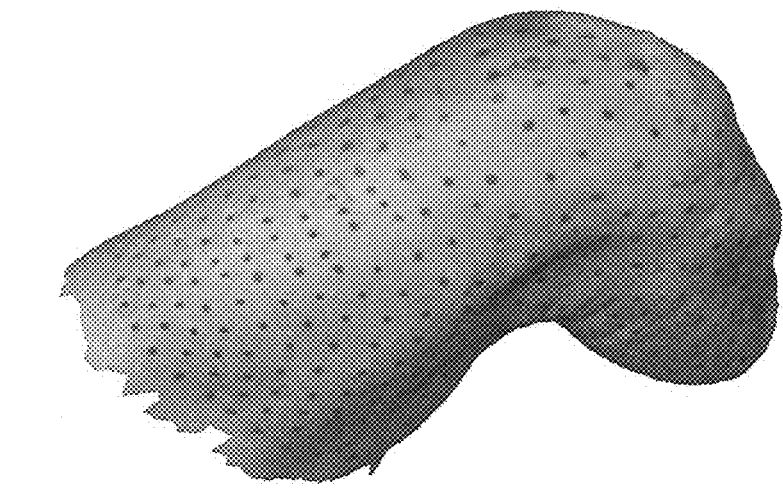
FIGS. 6A-6C represent three poses of a transtibial residual limb are shown each corresponding to a particular knee flexion angle. Black dots mark the skin at a resolution of approximately 4 dots per cm$^2$.
Figure 6B:
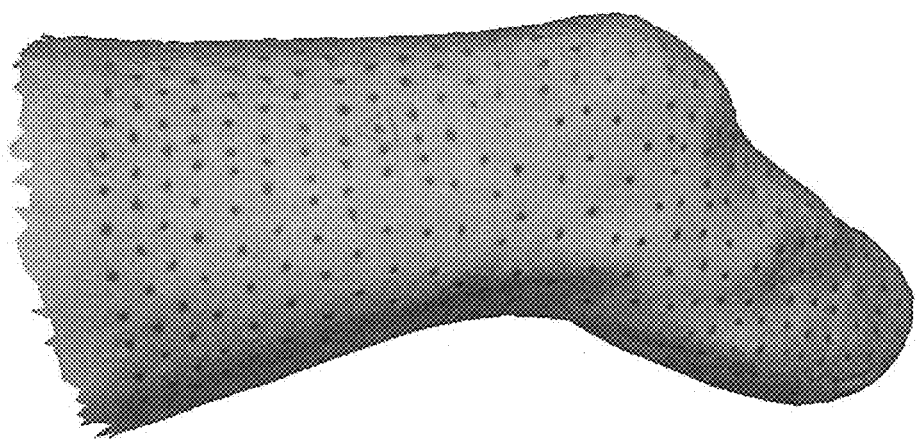
Figure 6A:
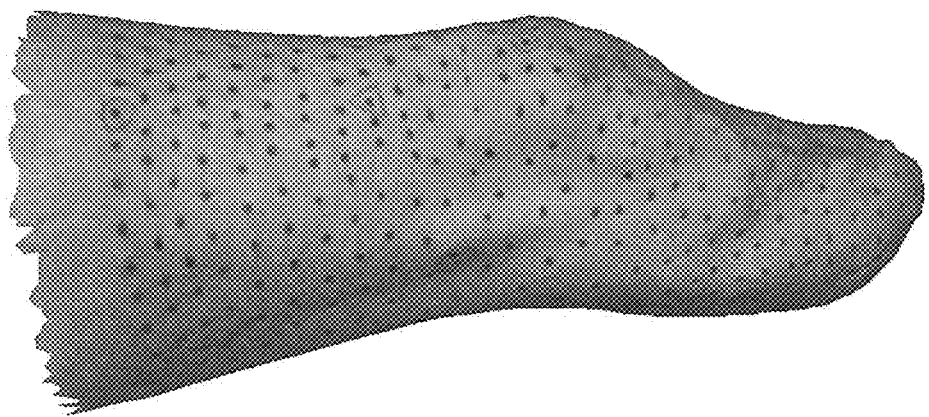
Figure 7C:
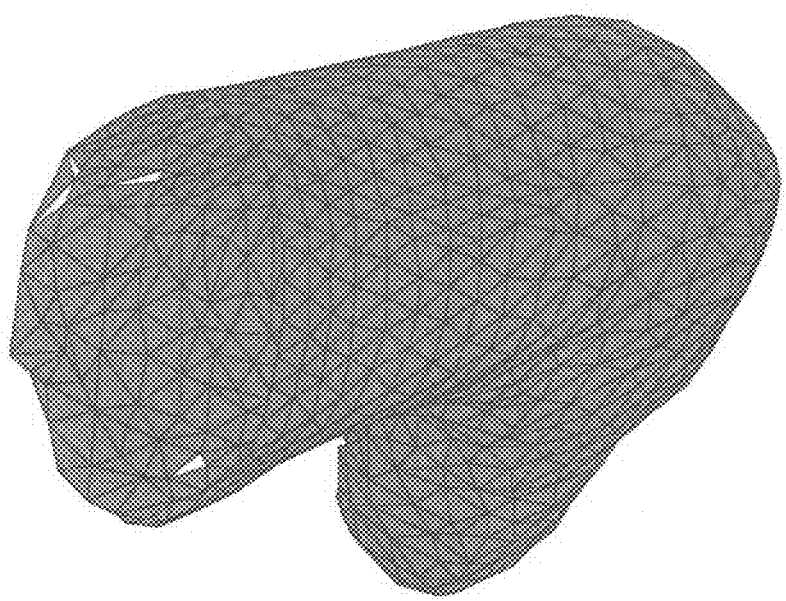
FIGS. 7A-7C represent the coordinate information from three triangulated poses of a transtibial residual limb are used to compute the strain transforms. A constant strain element analysis is performed on each triangle to ascertain the strain field of the limb's surface.
Figure 7B:
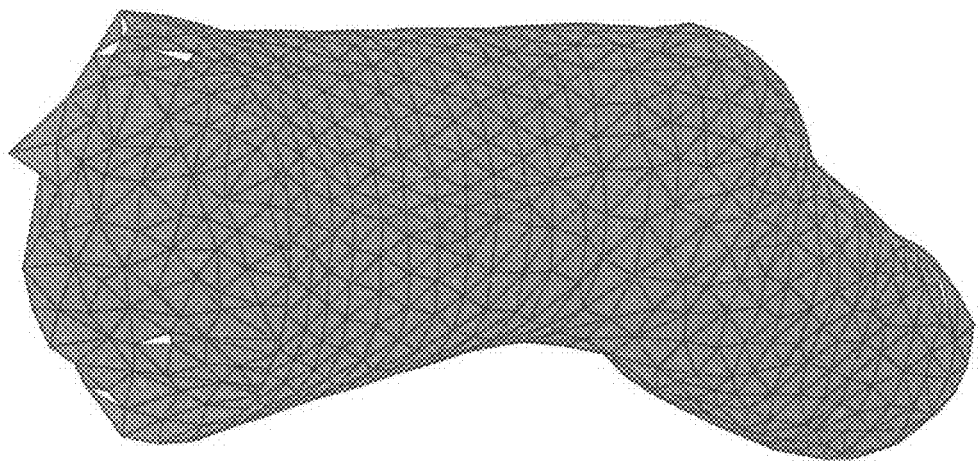
Figure 7A:
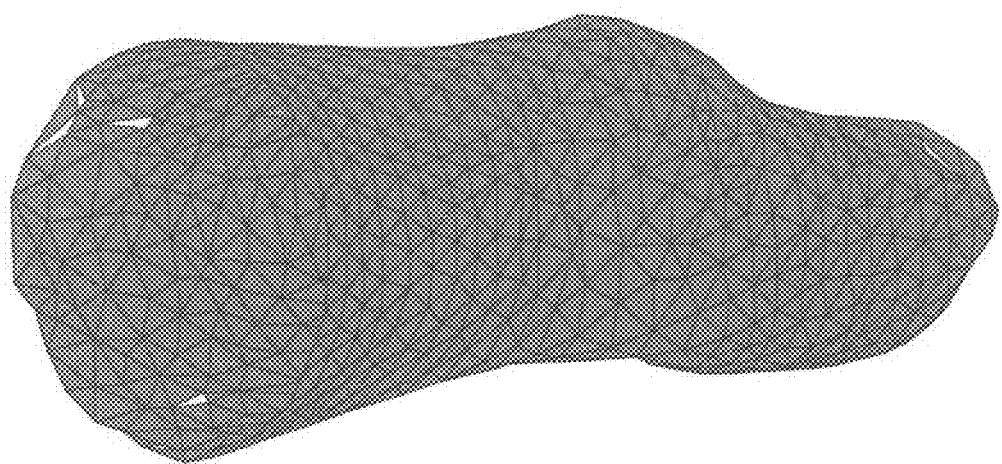

Skin Strain Model:

A skin strain model can be generated to understand how the mechanical interface should move and stretch relative to the skin surface, so as to minimize shear forces and discomfort at the skin-interface junction. In this procedure, the biological limb is first marked with a matrix of small (~2 mm diameter), black-ink dots across the entire skin-surface area for which the interface is designed to interact. The specific anatomical location and distance between these dots need not be precise, but the resolution, or the number of dots per $cm^2$ is important, as this resolution defines the resolution of the resulting skin strain field. In addition, the resolution can be variable, providing the opportunity to further investigate deformation in certain areas. Next, separate poses, or joint postures of the biological segment of interest, are captured using photogrammetric tools. Using approximately thirty digital photographs for each limb pose, 3D models are generated. The coordinates of the black dots on the skin are marked and exported for analysis. The point clouds for each pose are triangulated in a corresponding manner so the mapping of points to triangles is the same. In FIGS. 6A-6C, an example is shown for a trans-tibial amputee's residual limb showing three levels of knee flexion, and a matrix of black dots across the skin surface. The black dots are the nodes of the finite element model and serve as the vertices for the surface triangulation. FIGS. 7A-7C shows the triangulated surface corresponding to the poses displayed in FIGS. 6A-6C.

The deformation of each triangular element from one pose to another is decomposed into a translation, rotation, and stretch via an affine transform. The three initial coordinate pairs $(x_i, y_i)$ and three final coordinate pairs $(x_f, y_f)$ are used to find the affine transform linking the two configurations. Equation 1 represents the affine transformation matrix that links the point sets for each element. The rigid body translation from the initial to the final pose ($\Delta x, \Delta y$) is neglected as it has no effect on the strain within the element.

$$\begin{bmatrix} x_f \\ y_f \\ 1 \end{bmatrix} = \begin{bmatrix} & & \Delta x \\ & A & \\ & & \Delta y \\ 0 & 0 & 1 \end{bmatrix} \begin{bmatrix} x_i \\ y_i \\ 1 \end{bmatrix} \quad (1)$$

Matrix A is a 2×2 matrix that contains the information about how a particular triangle is rotated and stretched. A singular value decomposition (SVD) of matrix A isolates the components of the deformation as described by equation 2. The SVD interprets the transformation as a rotation V* to the principal coordinate frame, followed by a stretch Σ along those axes, and an additional rotation U to the final coordinate frame.

$$A = U\Sigma V^* \qquad (2)$$

Figure 8B:
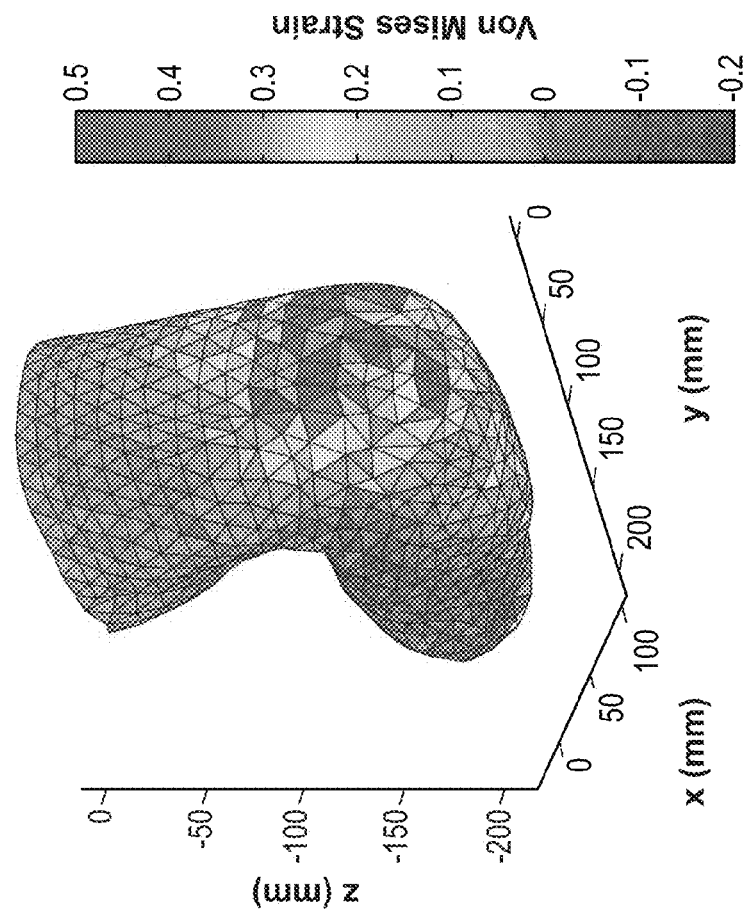
FIGS. 8A and 8B represent average strain of each triangular face as analyzed and mapped to color. Skin strain levels are shown for the partially flexed pose (FIG. 8A) and fully flexed pose (FIG. 8B). Higher average strain is shown around the knee patella due to the right poses increased knee flexion.
Figure 8A:
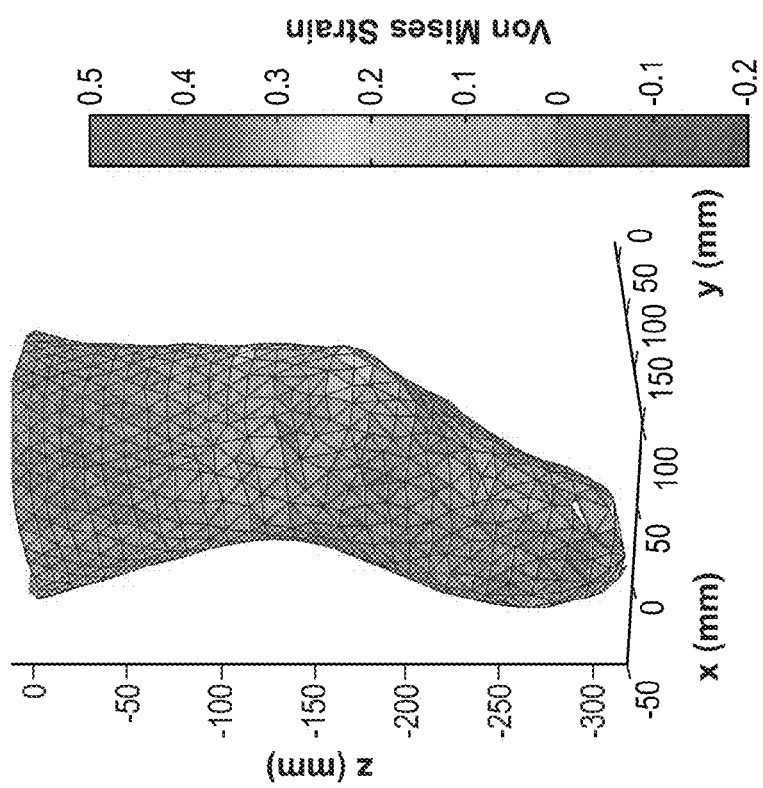

The stretch matrix Σ yields the principal strains which are used to compute the average strain of each constant strain triangle. Equation 3 computes the von Mises or equivalent strain $\varepsilon_e$ from the principal strains, $\varepsilon_1$ and $\varepsilon_2$. FIGS. 8A and 8B shows the equivalent strain of each triangulation resulting from the deformation of the original, extended pose to two different levels of knee flexion. The average strain is a scalar value that is useful for assessing the overall stretch of an element.

$$\varepsilon_e = \frac{1}{2}\sqrt{(\varepsilon_1 - \varepsilon_2)^2 + \varepsilon_1^2 + \varepsilon_2^2} \qquad (3)$$

Figure 9A:
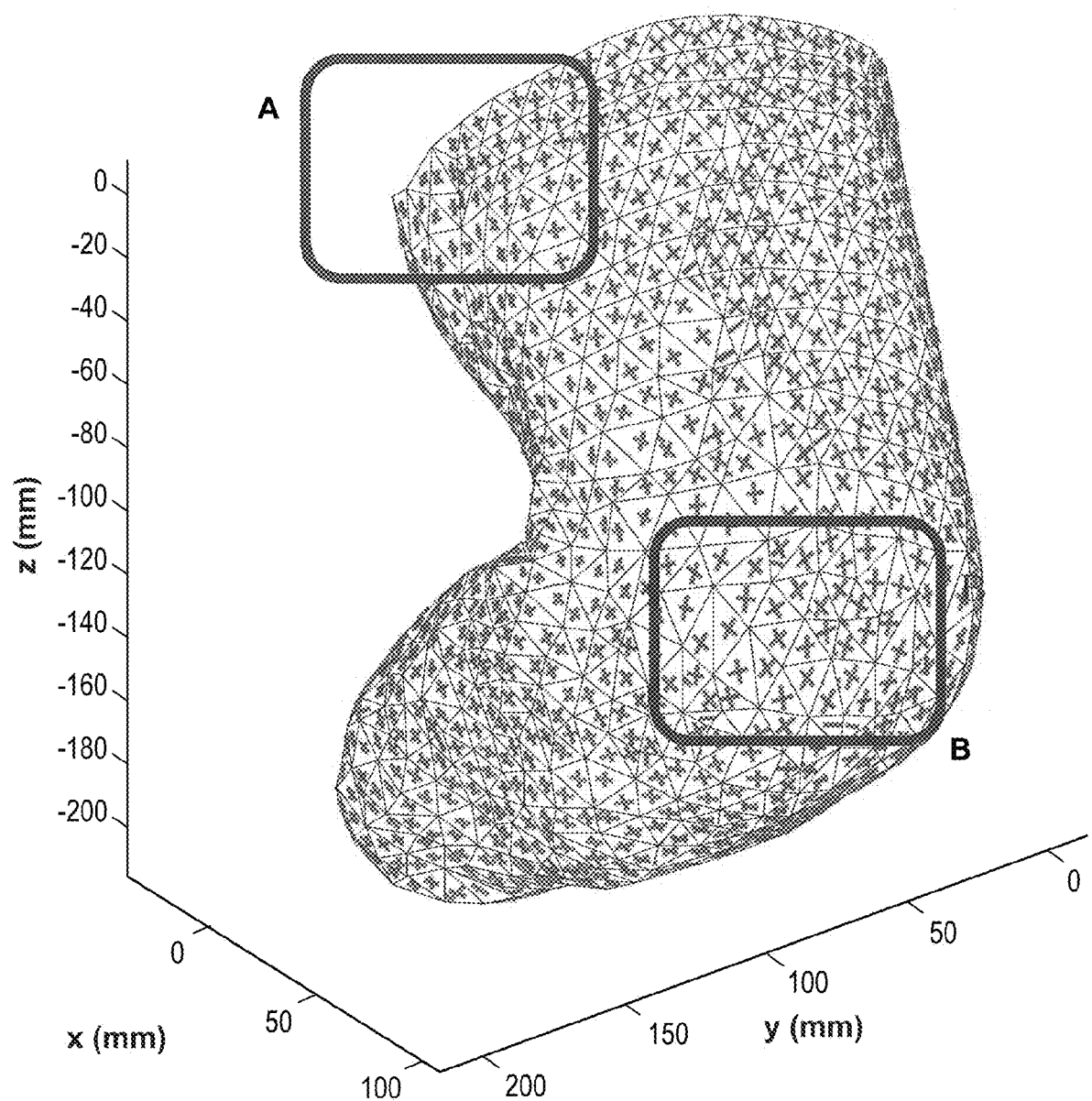
FIGS. 9A and 9B represent strain field of the knee flexed to approximately 90°. The larger (red) strain field is nearly horizontal proximal to the knee joint as the skin stretches.
Figure 9B:
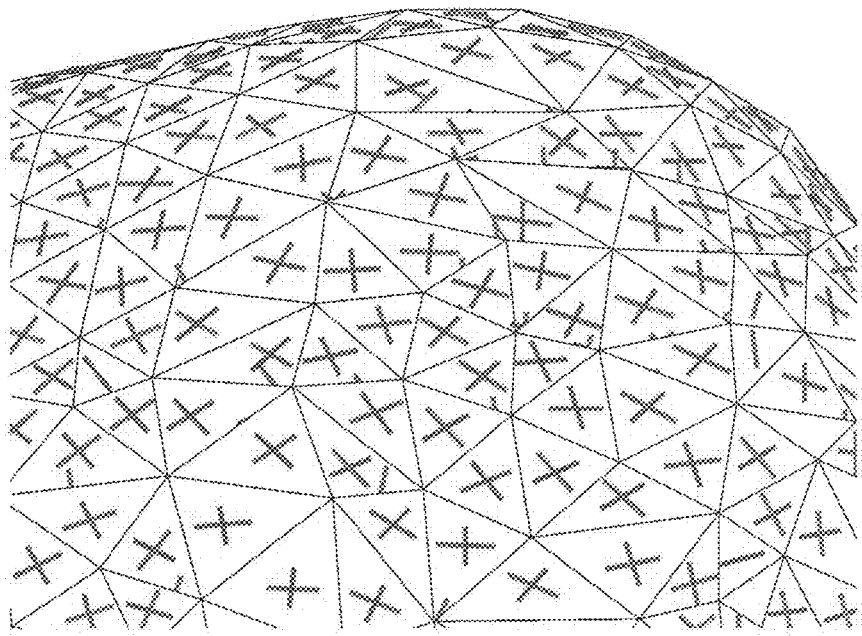
Figure 9B:
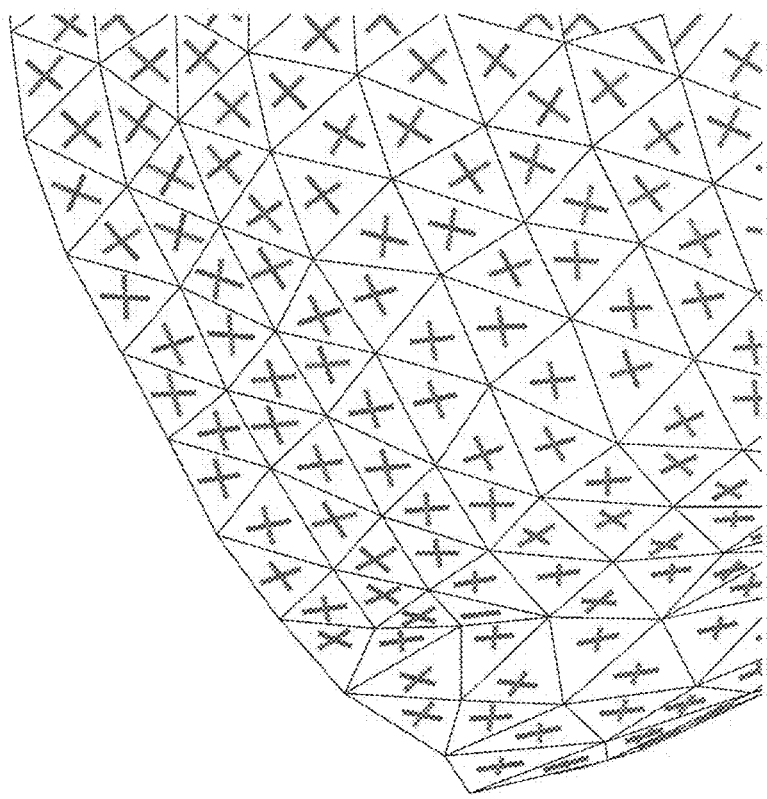

Furthermore, the strain state of each two-dimensional surface element can be derived from Mohr's circle using the principal strain information. This maps the two principal strains to a combination of normal and shear strains in another coordinate frame. The strain field can be computed using the information from the SVD of each triangle. FIGS. 9A and 9B plot the strain field for the particular case of a transtibial amputation. The red vectors represent the direction and magnitude of the larger of the two normal strains of each triangle. The blue vectors represent the smaller strain. Any shear strain is represented by the angle between the corresponding red and blue vectors of a particular triangular element. The strains throughout each triangle are assume to be constant and are therefore plotted at the centroid of each triangle. If a high enough dot resolution is used, a constant strain element analysis is sufficient to assess the strain state of a deformed surface.

Biological-Limb Shape and Impedance Model:

After the biological limb is captured using photogrammetric tools, the biological limb of interest can be imaged with a MRI machine and/or an electromechanical device can be used for measuring biological-limb, viscoelastic tissue properties and shape. Once these additional data are collected, a grid of resolution matched to the skin of the patient (e.g. average 1×1 cm) is established where a node of known variables is created around each grid or averaged for a defined grid. Alternatively, the grid could correspond to the grid of skin-strain triangles, for which FIGS. 9A and 9B provide an example, where a node is the center point within each respective triangle. Each anatomical node vector V(i) has properties including, but not limited to, anatomical 3D location with no tissue load, maximal skin tensile strain due to joint movement, orthogonal compression stiffness K and damping B as a function of tissue compression and compression rate, and the sensitivity to externally-applied pressure influenced by the underlying anatomy. Here the compression stiffness and damping, or orthogonal impedance, is defined as the biological limb's response to a displacement impulse perpendicular to the skin at each node. Further, the maximum skin tensile strain is computed as the average strain of the three legs of the corresponding strain triangle (FIGS. 8A and 8B).

Figure 10C:
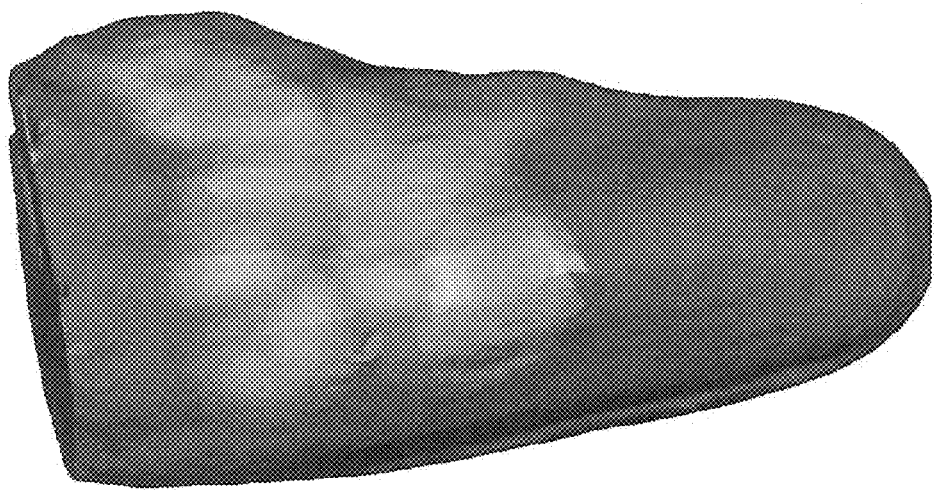
FIGS. 10A-10C represents 3-D images of bones and soft tissue depth shown for the right vestigial limb of a trans-tibial amputee.
Figure 10B:
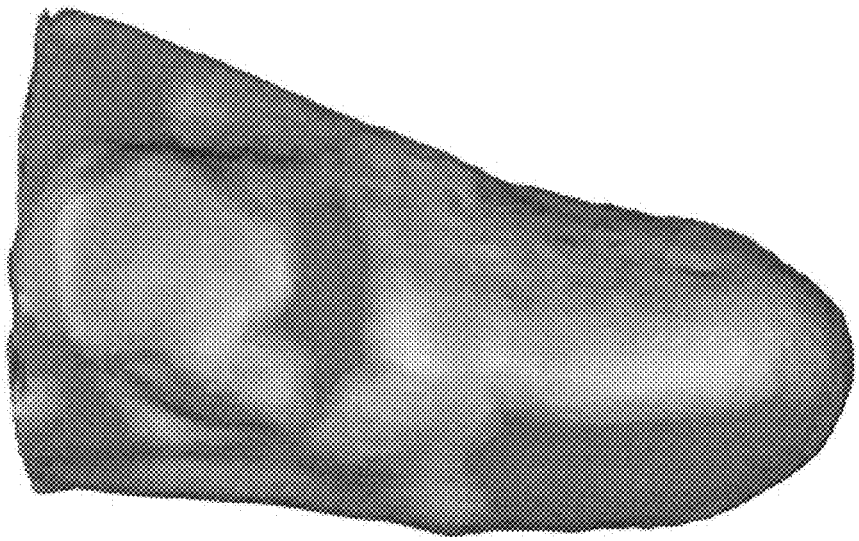
Figure 10A:
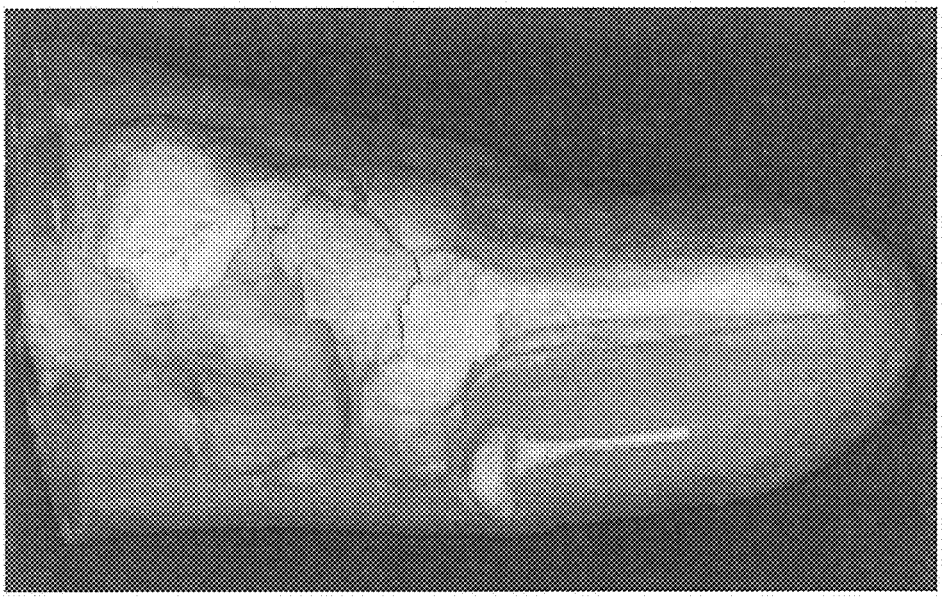

As an example, FIGS. 10A through 10C show a simple model of the residual limb of a trans-tibial amputee generated from MRI data. The model provides the unloaded shape and soft tissue depth of the residual limb as a function of anatomical location. Here soft tissue depth, D, is defined as the perpendicular distance from a node skin surface area and the intersection of that line with a bone. Although soft tissue depth correlates approximately to body stiffness, K, it is understood that a more sophisticated modeling exercise of soft tissue biomechanics would produce a more precise model of the residual limb's compression stiffness, K, and damping, B, properties as a function of anatomical location and neural activation. Here neural activation is included since large changes in viscoelastic properties occur depending upon whether muscles are activated or relaxed. Such a biological segment model would also include information on the locations of nerve and veins, and their relative pressure tolerances.

STEP 3: The characterized representation of the body segment formed by processing the compiled data set is then quantitatively mapped to form a digital representation of shape and impedance of a mechanical interface.

Mapping Skin Strain Model to the Tensile Viscoelastic Properties of the Mechanical Interface:

In the case of a transtibial leg amputation, FIGS. 9A and 9B clearly show relatively large longitudinal skin strain at, and just proximal to, the patella, as well as large circumferential strains proximal to the knee joint when the knee assumes a flexed posture. Using conventional prosthetic socket technology, an amputee typically wears a liner that is rolled across the residual limb. By making the coefficient of static friction high between the skin and liner materials, designers have effectively lowered relative movement at that interface, reducing uncomfortable rubbing and chaffing. However, current liner technology does not comprise continuously varying tensile material properties that are informed by a skin-strain model as described in the previous section. Consequently, in areas of large skin strain, inflexibility in the liner causes skin discomfort due to high skin shear stresses imposed by the liner material. For example, in the case of a transtibial amputation, inflexibility in the liner in the high strain regions, or the patella and proximal knee areas, cause skin discomfort, especially when an amputee sits with knees flexed for an extended period of time.

In one embodiment of the present invention, a liner that applies minimal shear stress on the skin when the biological segment changes posture, minimizing discomfort at the skin-interface junction. Specifically, mechanical strain energy stored within the liner is minimized when the biological limb is moved to a pose with large skin strains by continuously adjusting the tensile viscoelastic properties of the material spatially across the liner surface.

As an example, for the case of a trans-tibial amputation as shown in the skin-strain model of FIGS. 9A and 9B, large tensile skin strains are clearly visible longitudinally at, and proximal to, the knee patella. In this region of the residual limb, the skin-strain triangles are stretched longitudinally, or along the long axis of the thigh, indicative of the skin being under a large tensile stretch in that direction (detail B). In this region, the liner should be more stiff along the directions of minimum strain, indicated by the blue vectors, and less stiff along the red vectors representing maximum strain. This serves to support the knee around the patella but permit knee flexion. In addition, due to muscle contractions upon knee flexion, large tensile skin strains are clearly visible circumferentially in the region of the leg proximal to the knee joint (detail A). Here, the proposed liner should permit circumferential expansion of the limb and be stiffer along the thigh's axial direction. The corresponding liner material adjacent to these large skin strain directions would be fabricated with a proportionally-small stiffness and damping, or tensile impedance, so as to minimize the amount of shear forces against the skin when the knee is flexed. In this invention, we teach use of quantitative mapping from the skin-strain model to the corresponding tensile viscoelastic properties of the adjacent liner. In the skin-strain model described in the previous section, a line connects each black-dot to an adjacent black-dot. In the modeling methodology, a strain is computed for each of these dot-to-dot lines, forming a whole grid of interconnected triangles (FIGS. 9A and 9B). In one embodiment of the present invention, the impedance of the adjacent liner material to tensile stretch is numerically computed along the line between each set of two black-dot points, or each leg of a skin-strain triangle. The numerical relationship could be linear or nonlinear depending upon the type of mechanical interface, the region of the body for which an interface is to be constructed, and the specific needs of the user. In one embodiment, the mapping from the skin-strain model to the liner tensile viscoelastic properties is linear; liner stiffness along each leg of a skin-strain triangle is inversely proportional to the computed maximal skin strain, namely, where the skin strain is large, the corresponding tensile liner stiffness is small. Further, where the skin strain is small, the corresponding tensile liner stiffness is large. In one embodiment, in regions of large skin strain, a black-dot to black-dot stiffness equal to zero could be preferable, or alternatively a small stiffness that does not cause skin discomfort when the joint is held at a large-strain pose for an extended period of time.

Mapping the Biological-Limb Shape-and-Impedance Model to Mechanical Interface Shape-and-Impedance Properties: A Linear Model:

The human anatomy is complex and consists of multiple materials of different properties. For example, a transtibial residual limb consists of bones, (femur, tibia, fibula, and the patella), muscles (tibialis, gastrocnemius, peroneus longus, etc.) and other anatomical landmarks including, but not limited to, the tibial tuberosity, medial femoral condyle, lateral femoral condyle and the medial tibial flare. In one embodiment of the present invention we employ a quantitative mapping between the viscoelastic properties of the body when the body is compressed orthogonal to the skin surface, and the corresponding properties of the mechanical interface. For areas on the body for which an interface is to be designed, the underlying anatomical components and their viscoelastic properties are quantitatively related to the stiffness and damping of the adjacent mechanical interface. For one embodiment of the present invention, interfacing material is adjacent to each anatomical location with inverse stiffness and damping characteristics to that of the body. Although an inverse linear mapping algorithm is employed here, there could exist a nonlinear mapping including but not limited to parabolic, hyperbolic, trigonometric, exponential functions, and differential equations will create unique spatial material compositions within the mechanical interface for each anatomical location. The available tools are limited to automatically measure the body's stiffness and damping properties when a residual limb is compressed perpendicular to its skin surface. As such, in one embodiment of the present invention, we assume that the gross stiffness and damping properties of the body scale to the soft tissue depth at that anatomical point. Here soft tissue depth is defined as the orthogonal distance between the surface of the skin and the intersection of bone tissue when the body is not being compressed and is in a state of equilibrium. For boney protuberances such as the fibula head in the trans-tibial residual limb, the soft tissue depth is small and the body is stiff to orthogonal compression. In distinction, in the calf region the soft tissue depth is relatively larger and the body is relatively softer to orthogonal compression.

Figure 11:
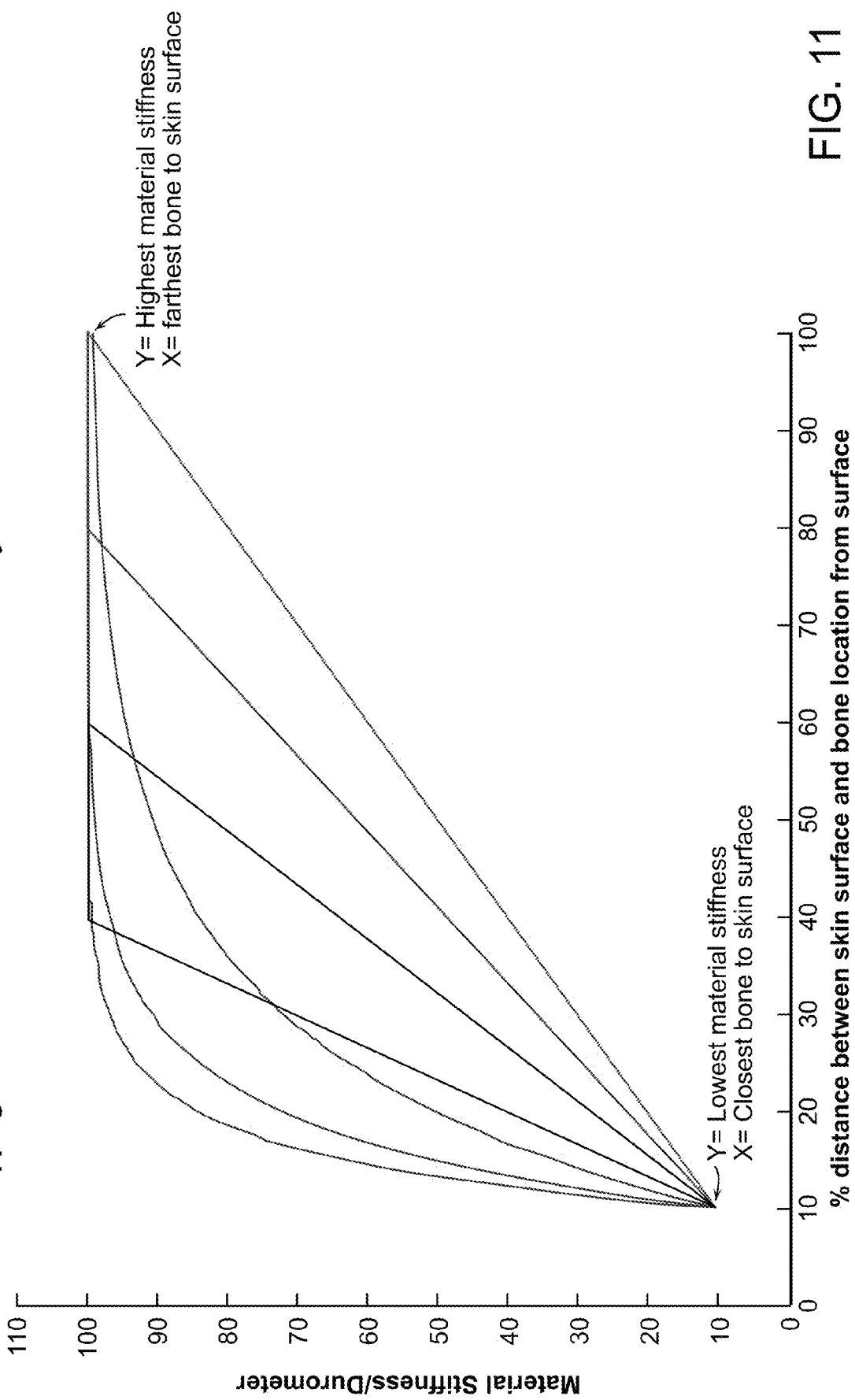
FIG. 11 is a plot showing linear and nonlinear relationships between a body segment and interface viscoelastic properties as estimated from soft tissue depth plotted horizontally, and the corresponding durometer of mechanical interface plotted vertically.

In one embodiment, the perpendicular distance from the skin surface to the bone obtained from MRI data is used as a gross estimate of the body's viscoelastic properties. FIG. 11 shows the quantitative relationship between mechanical interface stiffness, or durometer, and body stiffness represented as the percentage of soft tissue depth. Here the horizontal axis is the soft tissue depth, D, normalized by the maximal soft tissue depth, $D_{max}$, multiplied by 100. Both linear and non-linear curves are presented showing the possible variation in the relationship between interface durometer and corresponding soft tissue depth. Generally, as soft tissue depth decreases, and body stiffness increases, the adjacent interface becomes increasingly soft. Where there are boney protuberances, the adjacent interface will be soft and compliant, but where the body is soft with a large soft tissue depth, the adjacent interface is designed to be more rigid. Such an inverse relationship between body orthogonal impedance and interface orthogonal impedance results in a more uniform pressure field across the residual limb surface. It will be understood by those of skill in the art that the level of orthogonal interface impedance may depend upon anatomical location. For example, when there are underlying nerves and vessels that may be more sensitive to external pressure, interface orthogonal impedance will have to be reduced accordingly. A single curve mapping tissue orthogonal impedance to interface viscoelastic properties may not be universally applied across the entire residual limb, but may vary as a function of anatomical location. A plurality of curves (such as are shown in FIG. 11) may be required to fully capture the quantitative mapping between body impedance levels, interface impedance properties and anatomical location.

Figure 12:
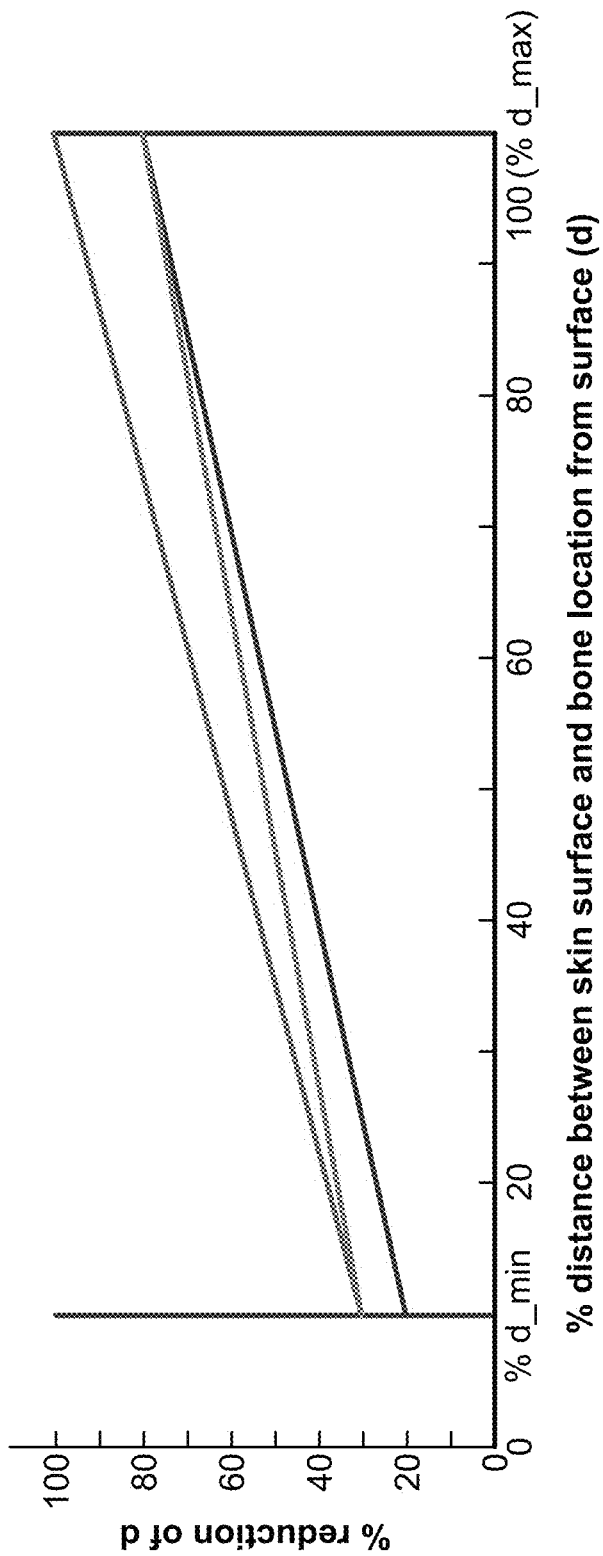
FIG. 12 is a plot showing relationships between an unloaded interface shape and soft tissue depth.
Figure 15A:
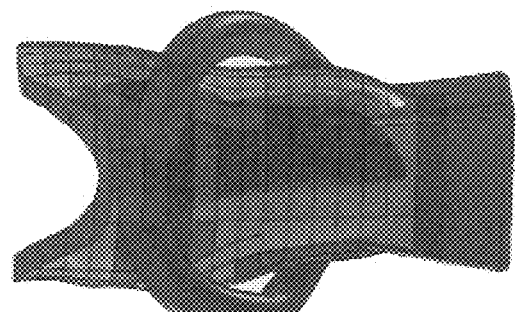
FIGS. 15A-15D represents a 3-D design of a variable viscoelastic socket showing, anterior, lateral, medial and posterior perspectives, respectively.
Figure 15B:
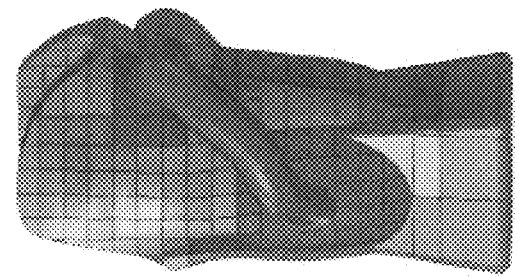
Figure 15C:
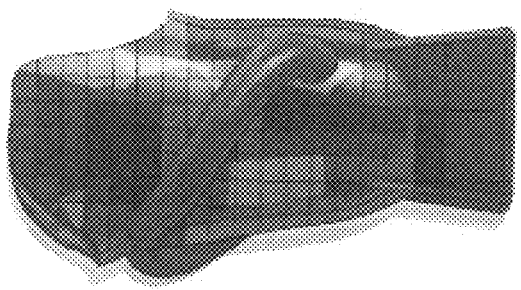
Figure 15D:
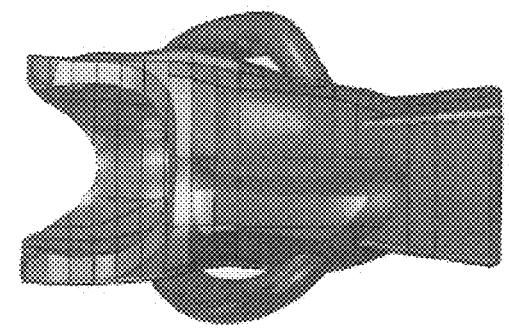
Figure 16A:
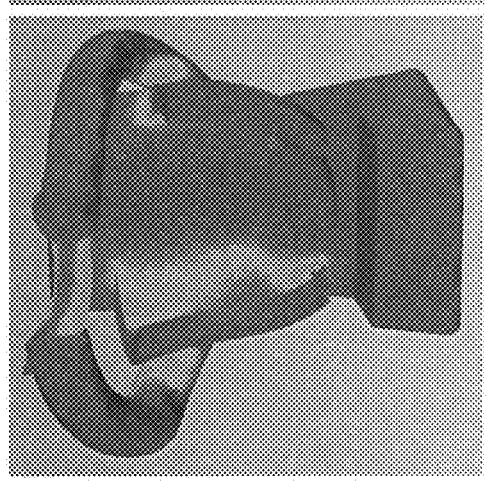
FIGS. 16A-16D represents finite element analyses of the socket represented in FIGS. 15A-15D, showing anterior, lateral, medial and posterior perspectives, respectively.
Figure 16B:
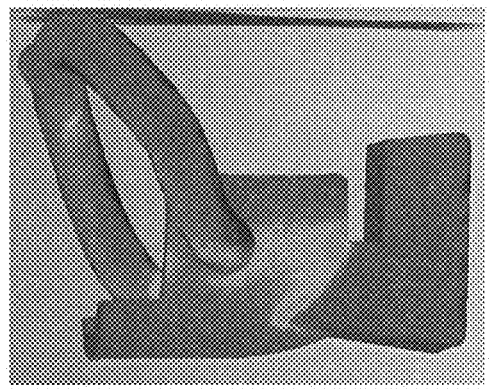
Figure 16C:
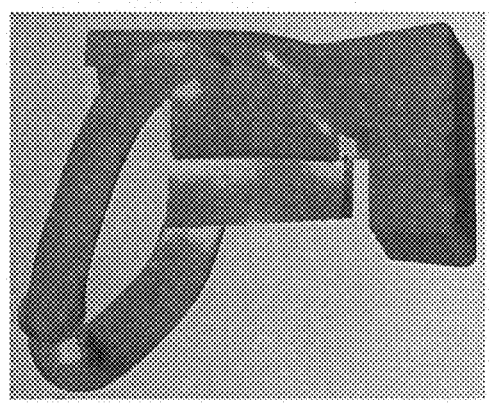
Figure 16D:
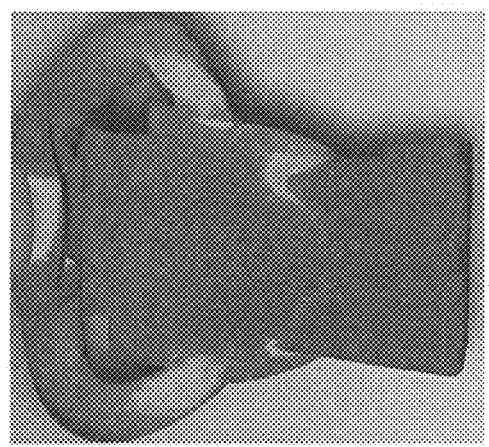

Another critical parameter that describes the mechanical interface design is the percent of soft tissue compression, namely the percent change in the soft tissue depth caused by the interface during a non-loaded state. In FIG. 12, the percent of soft tissue compression is plotted vertically, and the percent of tissue depth is plotted horizontally. Here the horizontal axis is the soft tissue depth, D, normalized by the maximal soft tissue depth, $D_{max}$, multiplied by 100. Further, the vertical axis is the soft tissue compression caused by the interface, normalized by the maximum soft tissue compression, multiplied by 100. Several linear curves are shown, depicting that as soft tissue depth increases, the amount that the interface compresses the tissue increases. Although only linear curves are shown in FIG. 12, additional embodiments could include nonlinear relationships such as parabolic, hyperbolic, trigonometric, exponential functions, and differential equations. Generally, where the body is soft, or where soft tissue depth is high, the interface will compress the tissues more. Where there is a boney protuberance, and the body is stiff with a small soft tissue depth, the interface will compress the tissues by a small amount or not at all. Such an inverse relationship between body stiffness and tissue compression results in a more uniform pressure field across the residual limb surface. It will be understood by those of ordinary skill in the art that the level of tissue compression by the interface may depend upon anatomical location. For example, when there are underlying nerves and vessels that may be more sensitive to external pressure, the level of tissue compression by the interface will have to be reduced accordingly. A single curve mapping the level of tissue compression to body viscoelastic properties may not be universally applied across the entire residual limb, but may vary as a function of anatomical location. A plurality of curves may be required to fully capture the quantitative mapping between tissue compression levels, body viscoelastic properties and anatomical location.

Mapping the Biological—Limb Shape and Impedance Model to Mechanical Interface Shape and Impedance Properties: A Optimization Procedure Previously, linear mappings (FIGS. 11 and 12) were assumed, relating the output of the shape-and-impedance biomechanical model to a numerical description of the interface's shape and impedance properties. In one embodiment of the invention, a mathematical optimization framework defines mapping that does not assume linearity a priori. The framework employs the digital anatomical data of that part of the body for which an interface design is sought, to attain that interface shape and impedance that produces a uniform interface pressure applied to the biological limb, and a minimized spatial pressure differential in the presence of atrophy by the biological limb.

An optimization procedure, employs key defined variables:

From a set of digital points $\vec{S}_i^v(X,Y,Z)$ located on the surface of the biological limb to be interfaced with a mechanical device, create a 3D volume. Here Z is in the direction of the gravitational vector, whereas X and Y are perpendicular to the Z-axis and to each other.

From three neighboring points or vertices $\vec{S}_1^v(X,Y,Z)$, $\vec{S}_2^v(X,Y,Z)$, and $\vec{S}_3^v(X,Y,Z)$, define the area vector ($\vec{A}_i$) of each triangle, within the grid, directed outwardly and orthogonally from the surface of the biological limb. Note the origin of area vector $\vec{A}_i(X,Y,Z)$ is located at the center of area at point $\vec{S}_i(X,Y,Z)$.

Define the unit area vector as $\vec{e}_i = \vec{A}_i/A_i$, or the area vector divided by the magnitude of the area vector. This unit vector is directed outwardly and orthogonally from the center of area of the section defined by the three neighboring vertices $\vec{S}_1^v(X,Y,Z)$, $\vec{S}_2^v(X,Y,Z)$, and $\vec{S}_3^v(X,Y,Z)$.

Define the angle $\theta_i$ between the line of the unit area vector and the vertical Z-axis.

Define the total area at the top of the socket in the Z direction, or $A_{Z\_top}$. A simplified approach to estimate $A_{Z\_top}$ is to assume a circle defining a plane that is orthogonal to direction Z, with a diameter equal to the average diameter of the residual limb adjacent the socket's upper, or most proximal, brim or cutline. More rigorously, $A_{Z\_top}$ is the total area in the Z direction of the adjoining surface connecting the line around the residual limb surface at the upper, or most proximal, brim or socket cutline.

Calculate the uniform Pressure ($P_{uni}$) within the prosthetic socket. It is approximated as $P_{uni} = W/A_{Z\_top}$ for a transtibial or transfemoral socket for a person in quiet, single-leg standing with body weight W. Alternatively, as a worst case, one could assume a uniform pressure equal to $3W/A_{Z\_top}$. Here the factor of 3 is an estimate of the dynamic loading experienced during running Calculate the vector force ($\vec{F}_i$) parallel but oppositely directed from area vector ($\vec{A}_i$) from the uniform socket pressure ($P_{uni}$)

$$\vec{F}_i = -P_{uni} * \vec{A}_i$$

Determine the residual limb impedance $I_i$ with stiffness $K_i$ and damping $B_i$ components of each node point $\vec{S}_i(X,Y,Z)$ at the center of area $\vec{A}_i$ (impedance is based on the mechanical properties of skin, muscle, fat and bone measured in the direction of the applied Force vector, $\vec{F}_i = -P_{uni} * \vec{A}_i$)

Calculate $\vec{r}_i(\Delta X, \Delta Y, \Delta Z)$ to get the new point $\vec{S}_i(X,Y,Z)^*$. The 3D volume from the set of points $\vec{S}_i(X,Y,Z)^*$ determines an optimal shape of the socket at load $\vec{F}_i = -P_{uni} * \vec{A}_i$ that achieves a uniform-socket, residual-limb interface pressure.

$$\vec{r}_i = \vec{S}_i(X,Y,Z)^* - \vec{S}_i(X,Y,Z).$$

For one embodiment, we estimate $\vec{r}_i(\Delta X, \Delta Y, \Delta Z)$ by assuming a linear approximation for body stiffness, or $K_i = C_i * d_i$ where $d_i$ is the scalar soft tissue depth defined as the distance from the center of area at $\vec{A}_i$ on the surface of the residual limb at point $\vec{S}_i(X,Y,Z)$ to the surface of the bone measurable using MRI, and $C_i$ is a proportionality constant between body stiffness $K_i$ and the distance $d_i$. Thus, $\vec{r}_i = \vec{F}_i/(C_i * d_i)$.

The procedure thus far estimates the shape of the residual limb $\vec{S}_i(X,Y,Z)^*$ under a uniform pressure, $P_{uni}$, with a load at each node equal to $\vec{F}_i = -P_{uni} * \vec{A}_i$ and the amount of tissue compression at that load, or $\vec{r}_i = -P_{uni} * \vec{A}_i/(K_i)$. Using a simplified model for estimating body stiffness $K_i = C_i * d_i$, we have $\vec{r}_i = -P_{uni} * \vec{A}_i/(C_i * d_i)$. Since $P_{uni} = W/A_{Z\_top}$, $\vec{r}_i = -(W/(A_{Z\_top} C_i d_i)) * (\vec{A}_i)$. However, what is still unknown is the optimal interface impedance, or for a static load assuming quiet standing, the optimal interface stiffness $k_i$. In this example, the damping force term $b_i * \vec{V}_i$ is not a consideration since it is a statics problem with tissue compression velocity $\vec{V}_i$ equal to zero. To optimize the stiffness of the socket interface $k_i$ at each interfacing node $\vec{S}_i(X,Y,Z)^*$ at pressure $P_{uni}$ that yields a constant socket pressure in a variable-impedance socket, we minimize the pressure differential ($\delta P/\delta Z$), or the change in interface pressure along the surface of the residual limb in the Z direction in the presence of an atrophy or hypertrophy disturbance.

The socket interface stiffness $k_i$ describes the stiffness of the interface adjacent to node i.

The amount of interface elastic compression at node i is equal to:

$$\vec{s}_i = \vec{F}_i/k_i = (-P_{uni} * \vec{A}_i)/k_i = (-W/A_{Z\_top} * \vec{A}_i)/k_i$$

Consider that the residual limb has changed shape at the zero load condition from $\vec{S}_i(X,Y,Z)$ to $\vec{S}_i^d(X,Y,Z)$ due to residual limb atrophy or hypertrophy. We can define an atrophy or hypertrophy disturbance vector $\vec{a}_i$ as $$\vec{a}_i = \vec{S}_i^d(X,Y,Z) - \vec{S}_i(X,Y,Z).$$

In one embodiment, the disturbance vector is equal to:

$\vec{a}_i = -D_i * d_i * \vec{e}_i$ where $\vec{e}_i = \vec{A}_i/A_i$ defined earlier, $d_i$ is the soft tissue depth defined earlier, and $D_i$ is a proportionality constant. We assume here that the atrophy or hypertrophy disturbance is orthogonal to the residual limb surface at node i, and is proportional to the soft tissue depth at that point.

After the disturbance, the interface spring compression would be:

$\vec{T}_i = \vec{s}_i - \vec{a}_i - \Delta Z_i(\vec{g}/g)$ and the force at node i would be $\vec{F}_i = k_i [\vec{s}_i - \vec{a}_i - \Delta Z_i(\vec{g}/g)]$ Here $\Delta Z_i = [W - \Sigma_i [k_i(\vec{s}_i - \vec{a}_i) \cdot \vec{g}/g]] / [\Sigma_i [k_i \cos \theta_i]]$ After the disturbance, the pressure field is no longer uniform, and is equal to:

$P_i = \vec{F}_i/\vec{A}_i$

Minimize the pressure differential $$\frac{\partial P_i}{\partial Z}$$

in the Z affection along the surface of the body from node to adjacent node by varying node stiffnesses $k_i$
For the array of interface stiffnesses $k_i^{min}$ that minimize $$\frac{\partial P_i}{\partial Z}_{min},$$

identify $S_i(X,Y,Z)^{}$ that gives the new interface equilibrium (unloaded) shape, or $S_i(X,Y,Z)^{} = \vec{s}_i + \vec{S}_i(X,Y,Z)$ where $\vec{s}_i = \vec{F}_i / k_i = (-P_{uni} * \vec{A}_i) / k_i^{min} = (-W/A_{Z\_top} * \vec{A}_i)/k_i^{min}$ STEP 4: The mechanical interface is then fabricated corresponding to the digital representation of the mechanical interface shape and mechanical interface impedance to thereby form a mechanical interface connecting the body segment to the wearable device. In one embodiment, the mechanical interface is fabricated to essentially replicate the redistribution of markings that correspond to surface strain of the body segment caused by movement of the body segment, with tensile impedance optimized so as to minimize shear stress between the interface and the skin surface. In another embodiment, the mechanical interface is fabricated to correlate the distribution of viscoelastic properties of the body segment, whereby the range of pressure across the surface of the body segment is minimized.

For example, the most advanced prototyping and CAM technology on the market can be employed to seamlessly integrate spatially-varying viscoelastic properties into the mechanical interface design. It is understood by those of ordinary skill in the art that the final mechanical interface can be manufactured using both traditional and state-of-the-art methods including, but not limited to, casting, 3D printing, mechanical linkages of desperate materials and shape deposition manufacturing.

Fabrication of Tensile Impedance Properties:

It will be understood by those of skill in the art that liner impedance properties can be varied spatially in a number of ways, including but not limited to, varying liner thickness, density, material composition and type, and/or material structure (e.g. through the use of small material hinges across the liner surface). In one embodiment, liner thickness is varied to accomplish spatial viscoelastic or impedance variation. Here each strain triangle leg (as an example, see FIGS. 9A and 9B) has a corresponding thickness of the liner inversely proportional to the maximum skin-strain computed. In another embodiment, the numerical mapping computes the average of the three skin strains corresponding to each leg of a skin-strain triangle (an example is shown in FIGS. 8A and 8B), and then an inversely-proportional relationship defines the corresponding liner thickness adjacent that triangular region.

In another embodiment, a plurality of different material types are employed within the liner. Along each leg of a skin-strain triangle for which large strains occur, a thin compliant material is employed within the liner, while adjacent the small-strain leg of a skin-strain triangle a separate material is attached to further increase the liner thickness and stiffness in such regions. For example, in the trans-tibial residual limb case, shown in FIGS. 9A and 9B, for the area proximal to the knee joint the skin is stretched circumferentially but not longitudinally along the long axis of the thigh upon knee flexion. The adjacent liner could comprise of a thin compliant material spanning the entire region, and attached to it strips of added material running longitudinal to the long axis of the thigh. When the thigh muscles contract and expand upon knee flexion, and the skin stretches circumferentially, the thin, compliant liner material would accommodate this stretch with minimal shear force applied to the skin, while the longitudinal strips would add structural integrity to the liner interface. In distinction, for the patella, and the region just proximal to the patella, shown in FIGS. 9A and 9B, the skin stretches longitudinally but not circumferentially as the knee assumes a flexed posture. In such regions, the thin strips of added material would run circumferentially, while the underlying thin, compliant material would connect adjacent strips, allowing the skin to stretch longitudinally upon knee flexion with minimal shear stress applied to the skin.

Fabrication of Orthogonal Impedance Properties:

Various methods have been suggested to relieve pressure over bony protuberances and other anatomical landmarks in passive prosthetic sockets. In conventional approaches, different materials have been bonded or mechanically attached together to relieve pressure on anatomical protrusions. Other CAD/CAM methodologies include the use of double walls, variable thickness walls, and most recently, the creation of mechanical compliant features in a 3-D printing process.

In one embodiment of the present invention we employ variable impedances seamlessly integrated into socket production using advanced 3D printing technology. 3D printing has been used in design of medical technologies for decades. However, the methodologies and capabilities of the machines have continued to evolve. Objet Geometries Inc. (North America, 5 Fortune Drive, Billerica, Mass. 01821, USA, T: +1-877-489-944) produces the most advanced 3D printer that uses their PolyJet Matrix™ Technology. This technology enables different material durometers to be simultaneously jetted in the production of the same mechanical interface, allowing for spatially varying viscoelastic properties across the interface surface. With a 16-micron, high-resolution print layer, high dots-per-inch in both X and Y resolution, and an easy-to-remove support material property, this technology is ideal for the development of prosthetic and orthotic prototypes. A relatively large library of standard materials used by the Connex family of 3D printers. In addition, composite materials can be created to produce Digital Materials™ to give a wide range of material properties; a desirable feature in prosthetic and orthotic designs mapped from calculated biological limb stiffness and damping properties.

Shown in FIGS. 13A-13D, 14A-14D, 15A-15D and 16A-16D is an example of how a 3-D printing process can be employed in the fabrication of a prosthetic socket prototype for a transtibial amputee. In FIGS. 13A-13D and FIGS. 14A-14D, MRI images and corresponding soft tissue depth models are shown for the right leg of a transtibial amputee. Orientation from left to right for all images are anterior, lateral, medial and posterior, respectively. Acquired MRI data are used to design the varying viscoelastic features within the socket wall.

FIGS. 14A-14D show the soft tissue depth model of the residual limb. As defined earlier, the soft tissue depth is the orthogonal distance D between the skin surface and a bone intersection. Here, red regions show large tissue depths, yellow regions moderate depths, and green regions relatively smaller depths. For these depth models, the patella tendon was removed, exposing the soft tissue depth in the region of the patella tendon just distal to the patella (shown as the red region in the left-most image).

In FIGS. 15A-15D, a 3-D printed prosthetic socket is shown where every material color corresponds to a material having a distinct durometer and tensile strength. Here, the red material has the highest durometer and tensile strength, while the green material has the smallest durometer and tensile strength. More specifically, FIG. 17 shows the mapping from soft tissue depth to interface material tensile strength. All these distinct compression viscoelastic features are integrated together seamlessly so that the sockets are manufactured in one piece with limited post processing requirements.

Figure 18:
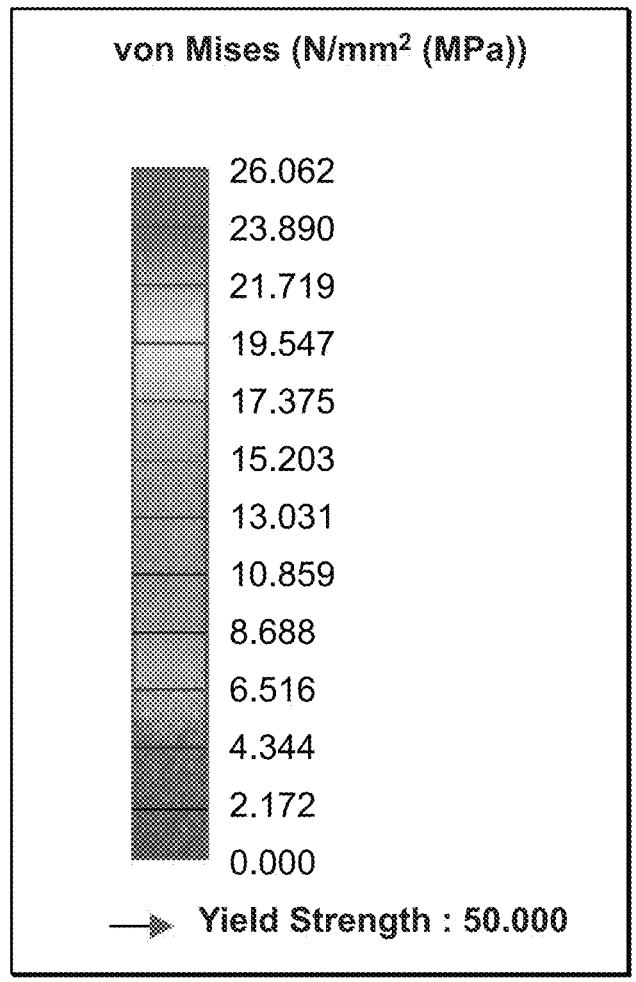
FIG. 18 is a von Mises Stress distribution for finite element analyses shown in FIGS. 16A-16D.

In FIGS. 16A-16D, the socket's most rigid, high tensile strength material (shown in red in FIGS. 15A-15D) is modeled using an FEA analysis to evaluate structural integrity for vertical loads comparable to that which would be experienced during standing and walking. FIG. 18 shows the Von Mises Stress distribution and corresponding color code used in FIGS. 16A-16D. Assuming a 3× body weight vertical loading, the wall thickness of the red material shown in FIGS. 15A-15D was varied to achieve an acceptable level of material stress. Additionally, the two struts, or bars, that connect the patella tendon region of the socket, having a relatively high impedance, to the distal socket base, having the same relatively high impedance, are included to achieve structural integrity; without these struts, the socket would be under risk of collapsing upon vertical loading when the amputee stood or walked with the socket interface.

Figure 19:
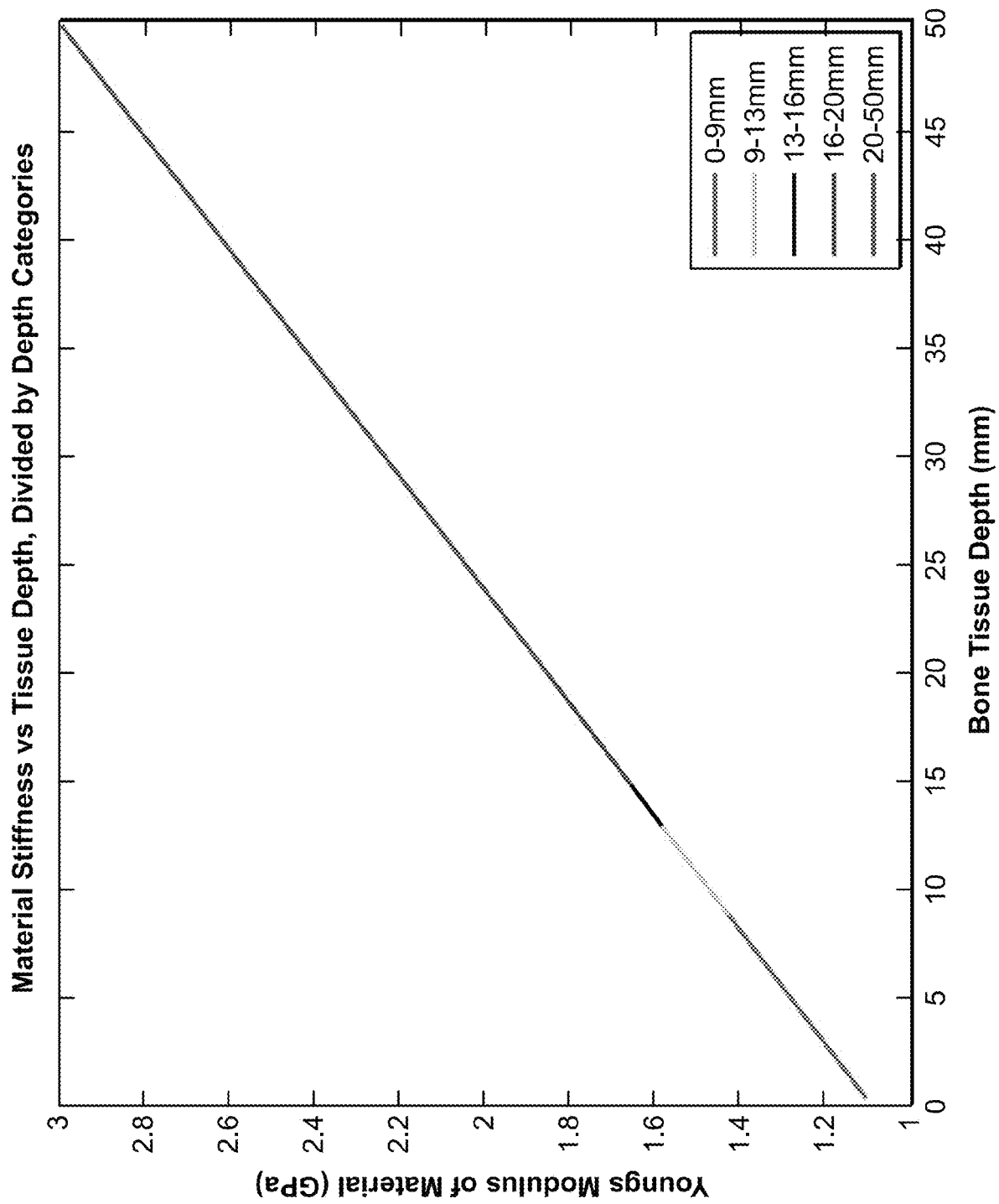
FIG. 19 is a plot representing mapping between the Youngs' modulus of socket interface materials shown in FIG. 15, to soft tissue depth at each location shown in FIG. 14. Color is coded by categories of soft tissue depth.

In FIG. 19, the linear relationship used in the socket design and fabrication of FIG. 15 is shown. Here the quantitative mapping of interface modulus (plotted vertically) to soft tissue depth (plotted horizontally) is plotted, showing numerically how the interface becomes softer and softer as the body becomes stiffer and stiffer (with smaller and smaller soft tissue depths).

The fabrication example shown in FIG. 17 can be problematic because the Objet 3-D printed material may be unstable, degrading in time with unfavorable mechanical properties. In this section, we propose a fabrication method that result in a more stable interface product.

From the optimized set of material impedances ($k_i$), a transformational mapping is established for manufacturing using conventional processes including, but not limited to, molding, casting, shape deposition, and carbon composite lamination. In FIG. 1, a trans-tibial socket is shown where each color represents a distinct material durometer or impedance. Such a variable-impedance socket layer can be fabricated using shape deposition processes or by modulating silicone durometer spatially using standard silicone fabrication procedures. The outer transparent element is designed to transfer load from the variable-impedance socket distally, while still allowing deformation of the compliant regions of the socket. This outer element can be made of carbon fiber and is used to ensure structural integrity while allowing flexibility in the regions where compliance is needed.

The ideal stiffness set $k_i$ for the mechanical interface can be produced with a spatially-varying impedance socket and integrated liner, encased in an outer carbon composite exoskeletal shell. In one embodiment of the present invention, a liner, or a thin polyurethane or silicone skin-tight sock, is bonded directly to the multi-material (FIG. 2) socket, or can be attached and removed easily in a donning and doffing process using standard attachment means such as a mechanical pin lock. In another embodiment of the invention, the liner and socket are fabricated as a single piece using polyurethane in a shape deposition process, or urethane using standard urethane fabrication strategies. Still further, in another embodiment the inner surface of the variable-impedance interface adheres to the body's skin using a synthetic "gecko" material that increases the shear strength between the skin and the interface, while still allowing easy donning and doffing of the artificial interface.

While this invention has been particularly shown and described with references to example embodiments thereof, it will be understood by those skilled in the art that various changes in form and details may be made therein without departing from the scope of the invention encompassed by the appended claims.

The relevant teachings of all references cited herein are incorporated by reference in their entirety.

What is claimed is:

1. A method for fabricating a mechanical interface for connecting a biological body segment to a wearable device, comprising the steps of:
    a) compiling a data set of features corresponding to a biological body segment;
    b) processing the compiled data set of features to thereby form a representation of tissue viscoelasticity of the biological body segment;
    c) quantitatively mapping the representation of the tissue viscoelasticity of the biological body segment to a digital representation of a mechanical interface shape and a mechanical interface impedance as a function of anatomical location at the biological body segment, the mechanical interface impedance including a representation of spatially-varying impedances of a material at an inner surface of the mechanical interface;
    d) optimizing the mechanical interface impedance in the digital representation to obtain an optimized digital representation, the optimizing including: determining a spatially varying plurality of impedance values that adjust a spatial pressure differential field along the inner surface of the mechanical interface as a function of anatomical location, determining a plurality of displacement values corresponding to the impedance values, and applying the displacement values to the digital representation to form the optimized digital representation; and
    e) fabricating a mechanical interface that includes a mechanical interface shape and a mechanical interface impedance that correspond to the mechanical interface shape and mechanical interface impedance of the optimized digital representation, the fabricated mechanical interface including a material having an impedance that varies spatially along an inner surface of the mechanical interface, thereby forming the mechanical interface for connecting the biological body segment to the wearable device.

2. The method of claim 1, wherein the data set is compiled by employing at least one method selected from the group consisting of casting, surface scanning, computerized tomography, magnetic resonance imaging, magnetic resonance elastography, ultrasound, photogrammetography and electromechanical measurement tools.

3. The method of claim 1, wherein the compiled data set is processed to generate at least one anatomical and biomechanical model of nodes of data, wherein each node includes a subset of data, the model collectively representing tissue impedance and at least one member of the group consisting of external biological body segment shape, soft tissue depth, tissue distribution, tissue density, tissue viscoelasticity, skin tensile strain, neural muscle activation and sensitivity to externally-applied pressure influenced by underlying anatomy of the body segment.

4. The method of claim 3, wherein the tissue impedance is computed by at least one member of the group consisting of orthogonal force, displacement and speed of displacement of the body segment, soft tissue depth, compression strain, and compression damping, and compression stiffness is computed at each node employed to generate the anatomical and biomechanical model.

5. The method of claim 3, wherein the subset of data of at least a portion of the nodes includes external biological body segment shape and orthogonal impedance of the body segment.

6. The method of claim 5, wherein the subset of data for each node is generated by conducting the steps of:
  a) marking a surface of the external biological body segment shape to form a detectable matrix of nodes;
  b) quantitatively mapping the nodes; and
  c) estimating orthogonal impedance of the body segment at each node.

7. The method of claim 6, wherein the mechanical interface is fabricated to correlate to a distribution of orthogonal impedance of the body segment.

8. The method of claim 7, wherein the orthogonal impedance of the interface surface is inversely proportional to the adjacent orthogonal impedance of the body segment.

9. The method of claim 8, wherein the inversely proportional relationship between interface impedance and body segment impedance is linear.

10. The method of claim 1, wherein the compiled data set is processed to generate at least one anatomical and biomechanical model of nodes of data, wherein each node includes a subset of data, the model collectively representing skin tensile strain and at least one member of the group consisting of external biological body segment shape, tissue orthogonal impedance, soft tissue depth, tissue distribution, tissue density, tissue viscoelasticity, neural muscle activation and sensitivity to externally-applied pressure influenced by underlying anatomy of the body segment.

11. The method of claim 10, wherein the generation of the skin strain model comprises the steps of:
  a) marking a surface of the body segment to form a detectable matrix of markings;
  b) quantitatively mapping the location of the markings;
  c) moving the body segment to thereby cause the markings to redistribute relative to each other; and
  d) quantitatively mapping the redistributed markings to thereby generate a three-dimensional image of redistribution of markings that corresponds to skin tensile strain of the body segment caused by the movement of the body segment.

12. The method of claim 11, wherein the three-dimensional image is a photogrammetric image.

13. The method of claim 12, wherein additional data are compiled from the body segment by magnetic resonance imaging.

14. The method of claim 13, wherein the body segment is at least a portion of a limb.

15. The method of claim 11, wherein the markings are processed as point clouds and wherein the point clouds are triangulated.

16. The method of claim 15, wherein the triangulated point clouds are processed by a constant strain element analysis.

17. The method of claim 11, wherein the mechanical interface is fabricated to essentially replicate the redistribution of markings that correspond to surface skin strain of the body segment caused by the movement of the body segment, in a manner that reduces skin shear stress across the interface.

18. The method of claim 17, wherein the tensile impedance of the interface surface is inversely proportional to an adjacent change in skin tensile strain caused by the movement of the body segment.

19. The method of claim 18, wherein the interface surface is defined by a liner, and wherein the wearable device includes the liner and a socket supporting the liner.

20. The method of claim 19, wherein the liner includes a relatively compliant material, proximate to portions of the body segment where relatively large skin tensile strains occur, and a relatively stiff material proximate to portions of the body segment where skin strains are relatively small.

21. The method of claim 20, wherein the liner includes strips of material running orthogonally to the general direction of skin tensile strain of a portion of the body segment most proximate to each individual strip.

22. The method of claim 1, wherein the wearable device is an orthotic device.

23. The method of claim 1, wherein the wearable device is a prosthetic device.

24. The method of claim 1, wherein the wearable device is an exoskeleton.

25. The method of claim 1, wherein the interface includes at least one strut extending from one interface area to another interface area.

26. The method of claim 1, wherein the mechanical interface for connecting the biological body segment to the wearable device includes a continuous socket defining a contoured inside surface and a contoured outside surface, wherein the socket includes a material having an intrinsic impedance that varies through the material, whereby the intrinsic impedance varies spatially along the contoured inside surface.

27. A method for fabricating a mechanical interface for connecting a biological body segment to a wearable device, comprising the steps of:
  a) compiling a data set of features corresponding to a biological body segment including a measurement of stiffness, to thereby obtain a measurement of tissue viscoelasticity of the biological body segment;
  b) processing the compiled data set of features to thereby form a representation of the biological body segment, the representation including a quantitative representation of mechanical impedance and shape of the biological body segment, the quantitative representation of mechanical impedance being derived, at least in part, from the measurement of the tissue viscoelasticity of the biological body segment;

c) quantitatively mapping the representation of the biological body segment to a digital representation of a mechanical interface shape and a mechanical interface impedance as a function of anatomical location at the biological body segment, the mechanical interface impedance including a representation of spatially-varying impedances of a material at an inner surface of the mechanical interface;

d) optimizing the mechanical interface impedance in the digital representation to obtain an optimized digital representation, the optimizing including: determining a spatially varying plurality of impedance values that adjust a spatial pressure differential field along the inner surface of the mechanical interface as a function of anatomical location, determining a plurality of displacement values corresponding to the impedance values, and applying the displacement values to the digital representation to form the optimized digital representation; and e) fabricating a mechanical interface that includes a mechanical interface shape and a mechanical interface impedance that correspond to the mechanical interface shape and mechanical interface impedance of the optimized digital representation, the fabricated mechanical interface including a material having an impedance that varies spatially along an inner surface of the mechanical interface, thereby forming the mechanical interface for connecting the biological body segment to the wearable device.

28. The method of claim 27, wherein the digital representation of mechanical interface impedance includes material stiffness.

29. The method of claim 27, wherein the mechanical interface for connecting the biological body segment to the wearable device includes a continuous socket defining a contoured inside surface and a contoured outside surface, wherein the socket includes a material having an intrinsic impedance that varies through the material, whereby the intrinsic impedance varies spatially along the contoured inside surface.

30. A method for fabricating a mechanical interface for connecting a biological body segment to a wearable device, comprising the steps of:

a) compiling a data set of features corresponding to a biological body segment;

b) processing the compiled data set of features to thereby form a representation of the biological body segment;

c) quantitatively mapping the representation of the biological body segment to form a digital representation of a mechanical interface shape and a mechanical interface impedance, the mechanical interface impedance including a representation of spatially-varying impedances of a material at an inner surface of the mechanical interface;

d) optimizing the mechanical interface impedance in the digital representation to obtain an optimized digital representation, the optimizing including: determining a spatially varying plurality of impedance values that adjust a spatial pressure differential field along the inner surface of the mechanical interface as a function of anatomical location, determining a plurality of displacement values corresponding to the impedance values, and applying the displacement values to the digital representation to form the optimized digital representation; and e) fabricating a mechanical interface that includes a mechanical interface shape and a mechanical interface impedance, wherein both the mechanical interface shape and the mechanical interface impedance are quantitatively determined by the optimized digital representation, the fabricated mechanical interface including a material having an impedance that varies spatially along an inner surface of the mechanical interface, to thereby form the mechanical interface for connecting the biological body segment to the wearable device.

31. A method for fabricating a mechanical interface for connecting a biological body segment to a wearable device, comprising the steps of:

a) compiling a data set of features corresponding to a biological body segment including a measurement of stiffness, to thereby obtain a measurement of tissue viscoelasticity of the biological body segment;

b) processing the compiled data set of features to thereby form a representation of the biological body segment, the representation including a quantitative representation of tissue viscoelasticity and shape of the biological body segment, the quantitative representation of mechanical impedance being derived, at least in part, from the measurement of the tissue viscoelasticity;

c) quantitatively mapping the representation of the biological body segment to form a digital representation of a mechanical interface shape and a mechanical interface impedance, the mechanical interface impedance including a representation of spatially-varying impedances of a material at an inner surface of the mechanical interface;

d) optimizing the mechanical interface impedance in the digital representation to obtain an optimized digital representation, the optimizing including: determining a spatially varying plurality of impedance values that adjust a spatial pressure differential field along the inner surface of the mechanical interface as a function of anatomical location, determining a plurality of displacement values corresponding to the impedance values, and applying the displacement values to the digital representation to form the optimized digital representation; and e) fabricating a mechanical interface that includes a mechanical interface shape and a mechanical interface impedance, wherein both the mechanical interface shape and the mechanical interface impedance are quantitatively determined by the optimized digital representation, the fabricated mechanical interface including a material having an impedance that varies spatially along an inner surface of the mechanical interface, to thereby form the mechanical interface for connecting the biological body segment to the wearable device.

* * * * *